(12) United States Patent
Sharratt et al.

(10) Patent No.: US 9,162,946 B2
(45) Date of Patent: Oct. 20, 2015

(54) PROCESS FOR PREPARING $C_{3-6}$ (HYDRO)FLUOROALKENES BY DEHYDROHALOGENATING $C_{3-6}$ HALO(HYDRO)FLUOROALKANES IN THE PRESENCE OF A ZINC/CHROMIA CATALYST

(71) Applicant: MEXICHEM AMANCO HOLDING S.A. DE C.V., Tlalnepantla (MX)

(72) Inventors: Andrew Paul Sharratt, Cheshire (GB); Leslie Richard Seddon, Cheshire (GB)

(73) Assignee: Mexichem Amanco Holding S.A. de C.V., Tlalnepantla (MX)

(*) Notice: Subject to any disclaimer, the term of this patent is extended or adjusted under 35 U.S.C. 154(b) by 0 days.

(21) Appl. No.: 14/043,191

(22) Filed: Oct. 1, 2013

(65) Prior Publication Data

US 2014/0031596 A1    Jan. 30, 2014

Related U.S. Application Data

(63) Continuation of application No. 12/311,540, filed as application No. PCT/GB2007/003749 on Oct. 3, 2007, now Pat. No. 8,546,623.

(30) Foreign Application Priority Data

Oct. 3, 2006  (GB) ................................... 0619505.1
Apr. 11, 2007 (GB) ................................... 0706980.0

(51) Int. Cl.
| | | |
|---|---|---|
| C07C 21/00 | (2006.01) | |
| C07C 17/04 | (2006.01) | |
| C07B 39/00 | (2006.01) | |
| C07C 17/20 | (2006.01) | |
| C09K 5/04 | (2006.01) | |
| C07C 17/275 | (2006.01) | |
| C07C 17/18 | (2006.01) | |
| C07C 21/18 | (2006.01) | |
| C07C 45/63 | (2006.01) | |
| C07C 17/087 | (2006.01) | |
| C07C 17/23 | (2006.01) | |
| C07C 17/25 | (2006.01) | |
| C07C 17/358 | (2006.01) | |

(52) U.S. Cl.
CPC .............. *C07C 17/23* (2013.01); *C07B 39/00* (2013.01); *C07C 17/04* (2013.01); *C07C 17/087* (2013.01); *C07C 17/18* (2013.01); *C07C 17/206* (2013.01); *C07C 17/25* (2013.01); *C07C 17/275* (2013.01); *C07C 17/358* (2013.01); *C07C 21/18* (2013.01); *C07C 45/63* (2013.01); *C09K 5/045* (2013.01); *C07B 2200/09* (2013.01); *C09K 2205/126* (2013.01)

(58) Field of Classification Search
CPC ........ C07C 17/23; C07C 17/25; C07C 17/358

USPC .......................................... 570/156, 158, 256
See application file for complete search history.

(56) References Cited

U.S. PATENT DOCUMENTS

| | | | |
|---|---|---|---|
| 2,700,686 A | 1/1955 | Dickey et al. | |
| 2,889,379 A | 6/1959 | Ruh et al. | |
| 2,918,501 A | 12/1959 | Brehm et al. | |
| 2,931,840 A | 4/1960 | Marquis | |
| 2,996,555 A | 8/1961 | Rausch | |
| 3,000,979 A | 9/1961 | Gibbs | |
| 3,398,204 A | 8/1968 | Gallant | |
| 3,674,665 A | 7/1972 | Cristol et al. | |
| 3,739,036 A | 6/1973 | Valicenti et al. | |
| 3,793,229 A | 2/1974 | Groppelli et al. | |
| 4,093,670 A | 6/1978 | Ozawa et al. | |
| 4,220,608 A | 9/1980 | Feiring | |
| 4,465,786 A | 8/1984 | Zimmer et al. | |
| 4,798,818 A | 1/1989 | Baizer et al. | |
| 5,616,819 A | 4/1997 | Boyce et al. | |
| 5,672,803 A | 9/1997 | Smith et al. | |
| 5,679,875 A | 10/1997 | Aoyama et al. | |
| 5,763,711 A | 6/1998 | Ito | |
| 5,811,603 A | 9/1998 | Elsheikh | |
| 5,856,593 A * | 1/1999 | Powell et al. ................ | 570/156 |
| 5,986,151 A | 11/1999 | Van Der Puy | |
| 6,111,150 A | 8/2000 | Sakyu et al. | |

(Continued)

FOREIGN PATENT DOCUMENTS

| | | |
|---|---|---|
| DE | 1140928 | 12/1962 |
| DE | 2128341 | 12/1971 |

(Continued)

OTHER PUBLICATIONS

Sianesi et al., Fluoroolefins-Report 1 Cis and trans 1,2,3,3,3-pentafluoropropylene, Soc Montecatini Milan, Ann Chim (Rome), 55(8-9), 850-861, 1965 (and English translation).
Journal of Fluorine Chemistry 1997; (82); p. 171-174.
Haszeldine R.N.; Fluoro-olefins. Part II: Synthesis and Reactions of Some 3,3,3,-Trihalogenopropenes; J.Chem.Soc., 1953, p. 3371-3378.
Advanced Organic Chemistry, (Ed. M.B. Smith and J. March), 5th edition, 2001, p. 1195.
Burton, D.J. et al., Preparation of E-1,2,3,3,3,-Pentafluoropropene, Z-1,2,3,3,3,-Pentafluoropropene and E-1 . . . ; Journal of Fluorine Chemistry; 1989; p. 167-174.
Buchner, M. et al; Reactions of Gaseous, Halogenated Propene Radial Cations with Ammonia: A Study; Chemistry: A European Journal, 1998, vol. 4, pp. 1799-1809.
Joyce R.M. et al., Free Radical-initiated Reaction of Ethylene with Carbon Tetrachloride; J. Am. Chem, Soc., 1948, pp. 2529-2532.

(Continued)

*Primary Examiner* — Sudhakar Katakam

(74) *Attorney, Agent, or Firm* — Ryan Kromholz & Manion, S.C.

(57) ABSTRACT

The invention relates to a process for preparing a C3-6 (hydro)fluoroalkene comprising dehydrohalogenating a C3-6 hydro(halo)fluoroalkane in the presence of a zinc/chromia catalyst, wherein the C¬ 3-6 (hydro)fluoroalkene produced is isomerised in the presence of the zinc/chromia catalyst.

21 Claims, 11 Drawing Sheets

(56) References Cited

U.S. PATENT DOCUMENTS

| | | | |
|---|---|---|---|
| 6,124,510 | A | 9/2000 | Elsheikh et al. |
| 6,329,559 | B1 | 12/2001 | Sievert et al. |
| 6,369,285 | B1 | 4/2002 | Mathieu et al. |
| 6,548,719 | B1 | 4/2003 | Nair et al. |
| 6,734,332 | B1 | 5/2004 | Slaugh et al. |
| 2005/0038302 | A1 | 2/2005 | Hedrick et al. |
| 2005/0090698 | A1* | 4/2005 | Merkel et al. ........... 570/155 |
| 2006/0122441 | A1 | 6/2006 | Tung |
| 2006/0269484 | A1 | 11/2006 | Knopeck et al. |
| 2007/0004585 | A1 | 1/2007 | Amos et al. |
| 2007/0100175 | A1* | 5/2007 | Miller et al. ............ 570/178 |
| 2007/0112230 | A1 | 5/2007 | Mukhopadhyay et al. |
| 2007/0129579 | A1 | 6/2007 | Wang et al. |
| 2007/0197842 | A1 | 8/2007 | Mukhopadhyay et al. |
| 2008/0051611 | A1 | 2/2008 | Wang et al. |
| 2008/0103342 | A1* | 5/2008 | Wang et al. ............. 570/256 |

FOREIGN PATENT DOCUMENTS

| | | |
|---|---|---|
| EP | 0097571 | 1/1984 |
| EP | 0169711 | 1/1986 |
| EP | 270006 | 6/1988 |
| EP | 0366797 | 5/1990 |
| EP | 0436989 | 7/1991 |
| EP | 0461297 | 12/1991 |
| EP | 0486333 | 5/1992 |
| EP | 0502605 | 9/1992 |
| EP | 0644173 | 3/1995 |
| EP | 0726243 | 8/1996 |
| EP | 0752403 | 1/1997 |
| EP | 0773061 | 5/1997 |
| EP | 0939071 | 9/1999 |
| EP | 0957074 | 11/1999 |
| EP | 1067106 | 1/2001 |
| EP | 1350564 | 10/2003 |
| EP | 1502906 | 2/2005 |
| EP | 1900716 | 3/2008 |
| EP | 1918269 | 5/2008 |
| FR | 2342952 | 9/1977 |
| GB | 1407696 | 9/1975 |
| JP | S 55130926 | 10/1980 |
| JP | 11140002 | 5/1999 |
| JP | 2005536424 | 12/2005 |
| JP | 2006503961 | 2/2006 |
| SU | 507551 | 5/1976 |
| WO | WO93/04025 | 3/1993 |
| WO | WO95/32935 | 12/1995 |
| WO | WO96/11896 | 4/1996 |
| WO | WO97/05089 | 2/1997 |
| WO | WO98/10862 | 3/1998 |
| WO | WO98/33756 | 8/1998 |
| WO | WO98/37043 | 8/1998 |
| WO | WO99/62857 | 12/1999 |
| WO | WO2004/018095 | 3/2004 |
| WO | WO2005/012212 | 2/2005 |
| WO | WO2005/023984 | 3/2005 |
| WO | WO2005/037431 | 4/2005 |
| WO | WO2005/037743 | 4/2005 |
| WO | WO2005/037744 | 4/2005 |
| WO | WO2005/042451 | 5/2005 |
| WO | WO2005/105947 | 11/2005 |
| WO | WO2005/108332 | 11/2005 |
| WO | WO2005/108333 | 11/2005 |
| WO | WO2005/108334 | 11/2005 |
| WO | WO2006/106353 | 10/2006 |
| WO | WO2007/019355 | 2/2007 |
| WO | WO2007/056128 | 5/2007 |
| WO | WO2007/056194 | 5/2007 |
| WO | WO2007/079431 | 7/2007 |
| WO | WO2007/145171 | 12/2007 |
| WO | WO2008/002500 | 1/2008 |
| WO | WO2008/008351 | 1/2008 |
| WO | WO2008/030443 | 3/2008 |
| WO | WO2008/040969 | 4/2008 |
| WO | WO2008/054781 | 5/2008 |
| WO | WO2008/054782 | 5/2008 |
| WO | WO2008/075017 | 6/2008 |
| WO | WO2009/140563 | 11/2009 |

OTHER PUBLICATIONS

Haszeldine et al; Carbene Chemistry. Part 11. Insertion Reactions of 1,2,2,-Trifluoroethylidene . . . ; J. Chem. Soc. Perkin Trans. 1, 1979, pp. 1943-1947.

Haszeldine et al; Free-radical Additions to Unsaturated systems, Part XVII. Reachtion of Trifluoroiodomethane with . . . ; J. Chem. Soc., 1970, pp. 414-421.

Haszeldine et al; Addition of Free Radicals to Unsaturated Systems. Part XXI. Reachtions of . . . ; J. Chem. Soc. Perkin Trans, 1, 1974, pp. 1303-1307.

Haszeldine et al; Fluoro-olefin Chemistry. Part X. Some additions to 1-Fluoropropene . . . ; J. Chem. Soc. Perkin Trans. 1, 1976, pp. 2349-2353.

Meyer et al:; Asymmetric Cyclopropanation of Vinyl Fluorides: Access to Enantiopure Monofluorinated Cyclopropane Carboxylates; Synthesis, 2000 pp. 1479-1490.

Atherton et al; Carbene Chemistry. Part II. Migration in Fluoroalkylcarbenes; J. Chem Soc; 1971, pp. 366-371.

Boche et al.; Stereospezifische Darstellung der (Z)~bzw. (E)~Isomeren von einigen Vinylfluoriden; J. Chem. Ber., 1981, pp. 4005-4009 English Abstract.

Baklouti et al.; Syntnese D'Ethyleniques Monofluores; J. Fluorine Chem.; 1981, pp. 181-190 English Abstract.

Banks R.E. et al; Preparation of 2,3,3,3-Tetrafluoropropene from Trifluoroacetylacetone and Sulphur Tetrafluoride; Fluoride Chem. (82), 1997, pp. 171-174.

Bartholomew, C.; Farrauto, R., Fundamentals of Industrial Catalytic Processes, 2nd ed., 2006, p. 285.

* cited by examiner

Fig. 1 Dehydrofluorination of CF$_3$CHClCH$_2$Cl at 15:1 HF:Orgs

Fig. 7 Impact of HF:organic on organic fouling rate in 236ea to Z-1225ye reaction - 340 C and 4.4 seconds.

PROCESS FOR PREPARING C$_{3-6}$ (HYDRO)FLUOROALKENES BY DEHYDROHALOGENATING C$_{3-6}$ HALO(HYDRO)FLUOROALKANES IN THE PRESENCE OF A ZINC/CHROMIA CATALYST

CROSS-REFERENCES TO RELATED APPLICATIONS

This application is a continuation of U.S. patent application Ser. No. 12/311,540 filed 16 Oct. 2009, now U.S. Pat. No. 8,546,623, issued 1 Oct. 2013, which was the US National Phase of PCT Application No. PCT/GB2007/003749 filed 3 Oct. 2007, which claimed priority to Great Britain application no. 0619505.1 filed 3 Oct. 2006 and Great Britain application no. 0706980.0 filed 11 Apr. 2007.

BACKGROUND OF THE INVENTION

The present invention relates to a process for preparing (hydro)fluoroalkenes and particularly to a process for preparing C$_{3-6}$ (hydro)fluoroalkenes by the dehydrohalogenation of a hydro(halo)fluoroalkane.

The known processes for preparing (hydro)fluoroalkenes typically suffer from disadvantages such as low yields, and/or the handling of toxic and/or expensive reagents, and/or the use of extreme conditions, and/or the production of toxic by-products. This is exemplified by considering the known methods for producing C$_{3-6}$ (hydro)fluoroalkenes such as 2,3,3,3-tetrafluoropropene. Methods for the preparation of 2,3,3,3-tetrafluoropropene have been described in, for example, Journal Fluorine Chemistry (82), 1997, 171-174. In this paper, 2,3,3,3-tetrafluoropropene is prepared by the reaction of sulphur tetrafluoride with trifluoroacetylacetone. However, this method is only of academic interest because of the hazards involved in handling the reagents and their expense. Another method for the preparation of 2,3,3,3-tetrafluoropropene is described in U.S. Pat. No. 2,931,840. In this case, pyrolysis of C1 chlorofluorocarbons with or without tetrafluoroethylene was purported to yield 2,3,3,3-tetrafluoropropene. However, the yields described were very low and again it was necessary to handle hazardous chemicals under extreme conditions. It would also be expected that such a process would produce a variety of very toxic by-products. In addition to addressing the disadvantages of the known methods, it would be desirable to provide new methods for the preparation of (hydro)fluoroalkenes that use only readily available feedstocks.

It is also known from U.S. Pat. No. 5,679,875 (Daikin) that 1,1,1,2,3-pentafluoropropene can be prepared by contacting and dehydrofluorinating 1,1,1,2,3,3-hexafluoropropane in the gaseous state with trivalent chromium oxide or partially fluorinated trivalent chromium oxide, optionally in the presence of oxygen.

The listing or discussion of a prior-published document in this specification should not necessarily be taken as an acknowledgement that the document is part of the state of the art or is common general knowledge.

SUMMARY OF THE INVENTION

The present invention addresses the foregoing deficiencies of the known routes for preparing (hydro)fluoroalkenes by providing a process for preparing a C$_{3-6}$ (hydro)fluoroalkene comprising dehydrohalogenating a C$_{3-6}$ hydro(halo)fluoroalkane in the presence of a zinc/chromia catalyst.

DESCRIPTION OF THE PREFERRED EMBODIMENT

Figure 1:
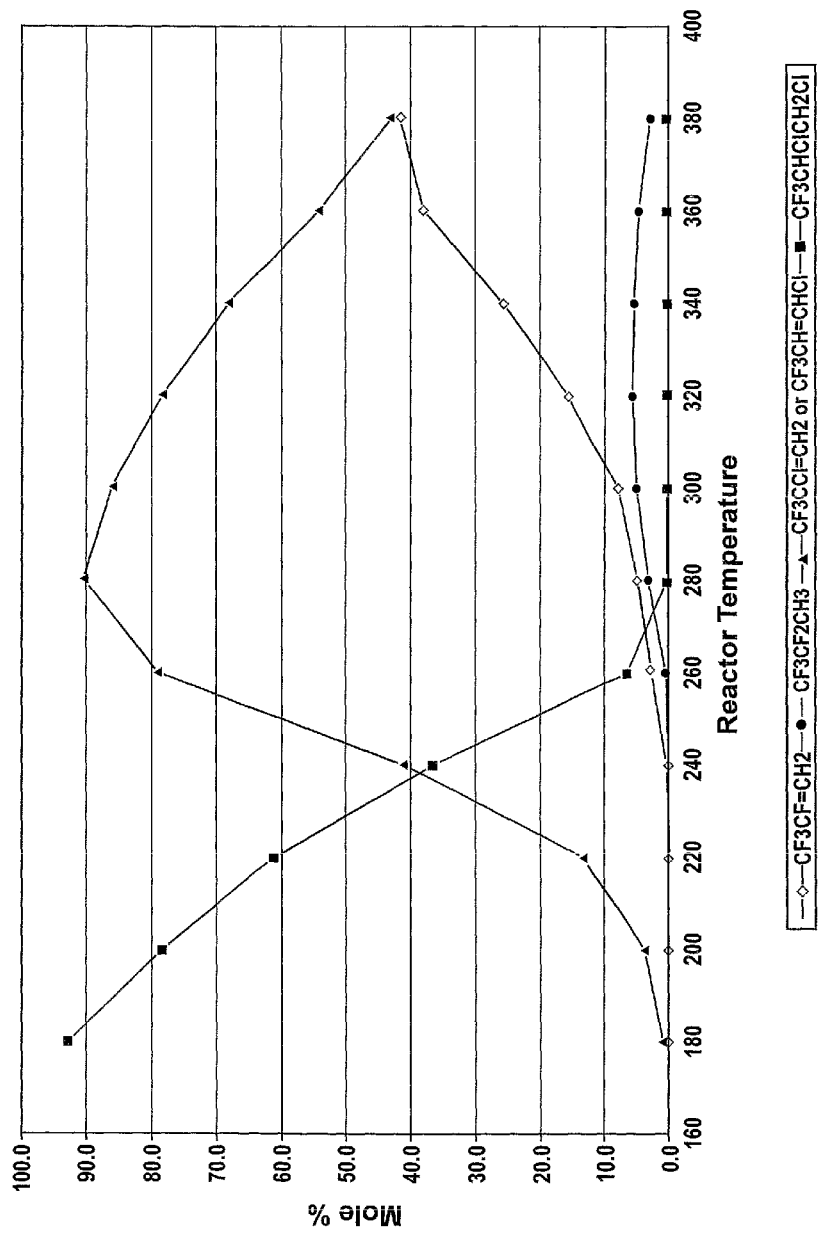
FIG. 1 is a graphical representation of the dehydrofluorination of CF3CFClCH2Cl at a 15:1 HF to Organics ratio at various reactor temperatures.

Typically, the process comprises contacting the hydro(halo)fluoroalkane with or without hydrogen fluoride (HF) in the vapour or liquid phase and may be carried out at a temperature of from −70 to 400° C. In certain preferred embodiments, the process may be carried out with no co-feed of HF. The process may be carried out at atmospheric sub- or super atmospheric pressure, preferably from about 0 to about 30 bara.

Preferably, the hydro(halo)fluoroalkane is contacted with or without HF in the vapour phase at a temperature of from 200 to 360° C., more preferably from 240 to 320° C. Preferably, the process is conducted at a pressure of from 5 to 20 bar. Of course, the skilled person will appreciate that the preferred conditions (e.g. temperature, pressure and catalyst) for conducting the process of the invention may vary depending on the nature of the hydro(halo)fluoroalkane being converted to (hydro)fluoroalkene. In certain preferred embodiments, for example where the catalyst contains 1% to 10% by weight of the catalyst of zinc, the process may be beneficially carried out at a pressure of 0 to 5 bara, conveniently 1 to 5 bara.

The process of the invention can be carried out in any suitable apparatus, such as a static mixer, a stirred tank reactor or a stirred vapour-liquid disengagement vessel. The process may be carried out batch-wise or continuously. Either the batch-wise process or the continuous process may be carried out in a "one-pot" fashion, or using two or more than discrete reaction zones and/or reaction vessels.

The dehydrofluorination can be carried out in the absence of HF but it may be desirable in certain embodiments to use some HF in order to prevent and/or retard excessive decomposition of the organic feed and/or coking of the catalyst. Typically, the HF:organics ratio in the process of the invention if HF is utilised will range from about 0.01:1 to about 50:1, preferably from about 0.1:1 to about 40:1, more preferably from about 0.5:1 to about 30:1, such as from about 1:1 to about 20:1, for example from about 2:1 to about 15:1 (e.g. from about 5:1 to about 10:1). The skilled person will appreciate that in a multi-stage process the preferred conditions and ratio may vary from step to step and would be able to select a suitable ratio.

The preferred aspects of the invention have been found to vary at least according to the nature of the catalyst, and the pressure at which the process is carried out.

By the term "zinc/chromia catalyst" we mean any catalyst comprising chromium or a compound of chromium and zinc or a compound of zinc. Such catalysts are known in the art, see for example EP-A-0502605, EP-A-0773061, EP-A-0957074 and WO 98/10862. However, the present inventors have surprisingly found that zinc/chromia catalysts may be used promote the dehydrohalogenation of $C_{3-6}$ hydro(halo)fluoroalkanes to produce $C_{3-6}$ (hydro)fluoroalkenes.

Typically, the chromium or compound of chromium present in the catalysts of the invention is an oxide, oxyfluoride or fluoride of chromium such as chromium oxide.

The total amount of the zinc or a compound of zinc present in the catalysts of the invention is typically from about 0.01% to about 25%, preferably 0.1% to about 25%, conveniently 0.01% to 6% zinc, and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst.

In other embodiments, the catalyst conveniently comprises 0.01% to 1%, more preferably 0.05% to 0.5% zinc.

The preferred amount depends upon a number of factors such as the nature of the chromium or a compound of chromium and/or zinc or a compound of zinc and/or the way in which the catalyst is made. These factors are described in more detail hereinafter.

It is to be understood that the amount of zinc or a compound of zinc quoted herein refers to the amount of elemental zinc, whether present as elemental zinc or as a compound of zinc.

The catalysts used in the invention may include an additional metal or compound thereof. Typically, the additional metal is a divalent or trivalent metal, preferably selected from nickel, magnesium, aluminium and mixtures thereof. Typically, the additional metal is present in an amount of from 0.01% by weight to about 25% by weight of the catalyst, preferably from about 0.01 to 10% by weight of the catalyst. Other embodiments may comprise at least about 0.5% by weight or at least about 1% weight of additional metal.

The zinc/chromia catalysts used in the present invention may be amorphous. By this we mean that the catalyst does not demonstrate substantial crystalline characteristics when analysed by, for example, X-ray diffraction.

Alternatively, the catalysts may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

During use in a dehydrohalogenation reaction the degree of crystallinity may change. Thus it is possible that a catalyst of the invention that has a degree of crystallinity as defined above before use in a dehydrohalogenation reaction and will have a degree of crystallinity outside these ranges during or after use in a dehydrohalogenation reaction.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (eg the graphite used in producing catalyst pellets) or more preferably by comparison of the intensity of the XRD patterns of the sample materials with reference materials prepared from suitable internationally recognised standards, for example NIST (National Institute of Standards and Technology) reference materials.

The catalysts of the invention typically have a surface area of at least 50 $m^2$/g and preferably from 70 to 250 $m^2$/g and most preferably from 100 to 200 $m^2$/g before it is subjected to pre-treatment with a fluoride containing species such as hydrogen fluoride or a fluorinated hydrocarbon. During this pre-treatment, which is described in more detail hereinafter, at least some of the oxygen atoms in the catalyst are replaced by fluorine atoms.

The catalysts of the invention typically have an advantageous balance of levels of activity and selectivity. Preferably, they also have a degree of chemical robustness that means that they have a relatively long working lifetime. The catalysts of the invention preferably also have a mechanical strength that enables relatively easy handling, for example they may be charged to reactors or discharged from reactors using known techniques.

The catalysts of the invention may be provided in any suitable form known in the art. For example, they may be provided in the form of pellets or granules of appropriate size for use in a fixed bed or a fluidised bed. The catalysts may be supported or unsupported. If the catalyst is supported, suitable supports include AlF3, fluorinated alumina or activated carbon.

The catalysts of the invention include promoted forms of such catalysts, including those containing enhanced Lewis and/or Brönsted acidity and/or basicity.

The amorphous catalysts which may be used in the present invention can be obtained by any method known in the art for producing amorphous chromia-based catalysts. Suitable methods include co-precipitation from solutions of zinc and chromium nitrates on the addition of ammonium hydroxide. Alternatively, surface impregnation of the zinc or a compound thereof onto an amorphous chromia catalyst can be used.

Further methods for preparing the amorphous zinc/chromia catalysts include, for example, reduction of a chromium (VI) compound, for example a chromate, dichromate, in particular ammonium dichromate, to chromium (III), by zinc metal, followed by co-precipitation and washing; or mixing as solids, a chromium (VI) compound and a compound of zinc, for example zinc acetate or zinc oxalate, and heating the mixture to high temperature in order to effect reduction of the chromium (VI) compound to chromium (III) oxide and oxidise the compound of zinc to zinc oxide.

The zinc may be introduced into and/or onto the amorphous chromia catalyst in the form of a compound, for example a halide, oxyhalide, oxide or hydroxide depending at least to some extent upon the catalyst preparation technique employed. In the case where amorphous catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of zinc and chromium may be co-precipitated (for example by the use of a base such as sodium hydroxide or ammonium hydroxide) and then converted to the oxides to prepare the amorphous catalyst. Mixing and milling of an insoluble zinc compound with the basic chromia catalyst provides a further method of preparing the amorphous catalyst precursor. A method for making amorphous catalyst based on chromium oxyhalide comprises adding a compound of zinc to hydrated chromium halide.

The amount of zinc or a compound of zinc introduced to the amorphous catalyst precursor depends upon the preparation method employed. It is believed that the working catalyst has a surface containing cations of zinc located in a chromium-containing lattice, for example chromium oxide, oxyhalide, or halide lattice. Thus the amount of zinc or a compound of zinc required is generally lower for catalysts made by impregnation than for catalysts made by other methods such as co-precipitation, which also contain the zinc or a compound of zinc in non-surface locations.

Any of the aforementioned methods, or other methods, may be employed for the preparation of the amorphous catalysts which may be used in the process of the present invention.

The catalysts described herein are typically stabilised by heat treatment before use such that they are stable under the environmental conditions that they are exposed to in use. This stabilisation is often a two-stage process. In the first stage, the catalyst is stabilised by heat treatment in nitrogen or a nitrogen/air environment. In the art, this stage is often called "calcination". Fluorination catalysts are then typically stabilised to hydrogen fluoride by heat treatment in hydrogen fluoride. This stage is often termed "pre-fluorination".

The present inventors have found that by careful control of the conditions under which these two heat treatment stages are conducted, crystallinity can be induced into the catalyst to a controlled degree.

For example, an amorphous catalyst may be heat treated at a temperature of from about 300 to about 600° C., preferably from about 400 to 600° C., more preferably from 500 to 590° C., for example 520, 540, 560 or 580° C. for a period of from about 1 to about 12 hours, preferably for from about 2 to about 8 hours, for example about 4 hours in a suitable atmosphere. Suitable atmospheres under which this heat treatment can be conducted include an atmosphere of nitrogen or an atmosphere having an oxygen level of from about 0.1 to about 10% v/v in nitrogen. Other oxidizing environments could alternatively be used. For example, environments containing suitable oxidizing agents include, but are not limited to, those containing a source of nitrate, $CrO_3$ or $O_2$ (for example air). This heat treatment stage can be conducted in addition to or instead of the calcining stage that is typically used in the prior art to produce amorphous catalysts.

Conditions for the pre-fluorination stage can be selected so that they do not substantially introduce crystallinity into the catalyst. This may be achieved by heat treatment of the catalyst precursor at a temperature of from about 200 to about 500° C., preferably from about 250 to about 400° C. at atmospheric or super atmospheric pressure for a period of from about 1 to about 16 hours in the presence of hydrogen fluoride, optionally in the presence of another gas such as nitrogen.

Conditions for the pre-fluorination stage can be selected so that they induce a change in the crystallinity of the catalyst or so that they do not induce such a change. The present inventors have found that heat treatment of the catalyst precursor at a temperature of from about 250 to about 500° C., preferably from about 300 to about 400° C. at atmospheric or super atmospheric pressure for a period of from about 1 to about 16 hours in the presence of hydrogen fluoride, optionally in the presence of another gas such as air, can produce a catalyst in which the crystallinity is as defined above, for example from 0.1 to 8.0% by weight of the catalyst (typically from 0.1 to less than 8.0% by weight of the catalyst) is in the form of one or more crystalline compounds of chromium and/or one or more crystalline compounds of the at least one additional metal.

The skilled person will appreciate that by varying the conditions described above, such as by varying the temperature and/or time and/or atmosphere under which the heat treatment is conducted, the degree of crystallinity of the catalyst may be varied. Typically, for example, catalysts with higher degrees of crystallinity (e.g. from 8 to 50% by weight of the catalyst) may be prepared by increasing the temperature and/or increasing the calcination time and/or increasing the oxidising nature of the atmosphere under which the catalyst pre-treatment is conducted.

The variation of catalyst crystallinity as a function of calcination temperature, time and atmosphere is illustrated by the following table showing a series of experiments in which 8 g samples of a 6% Zn/chromia catalyst were subjected to calcination across a range of conditions and the level of crystallinity induced determined by X-Ray diffraction.

| Calcination Time (t, hrs) | Calcination Temperature (T, ° C.) | Atmosphere nitrogen:air (D, v/v) | % Cryst $Cr_2O_3$ Content |
| --- | --- | --- | --- |
| 4 | 400.0 | 15 | 1 |
| 4 | 400.0 | 15 | 1 |
| 2 | 450.0 | 20 | 9 |
| 6 | 350.0 | 20 | 0 |
| 2 | 450.0 | 10 | 18 |
| 2 | 350.0 | 10 | 0 |
| 6 | 450.0 | 20 | 20 |
| 6 | 350.0 | 10 | 0 |
| 6 | 450.0 | 10 | 30 |
| 4 | 400.0 | 15 | 1 |
| 2 | 350.0 | 20 | 0 |

The pre-fluorination treatment typically has the effect of lowering the surface area of the catalyst. After the pre-fluorination treatment the catalysts of the invention typically have a surface area of 20 to 200 $m^2/g$, such as 50 to 150 $m^2/g$, for example less than about 100 $m^2/g$.

In use, the catalyst may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst.

Unless otherwise stated, as used herein, a (hydro)fluoroalkene is an alkene in which at least one of the hydrogen atoms has been replaced by fluorine.

Unless otherwise stated, as used herein, a hydro(halo)fluoroalkane is an alkane in which at least one but not all hydrogen atom has been replaced by a fluorine atom and optionally at least one hydrogen atom has been replaced by a halogen selected from chlorine, bromine and iodine. Thus, hydro(halo)fluoroalkanes contain at least one hydrogen, at least one fluorine and optionally at least one halogen selected from chlorine, bromine and iodine. In other words, the definition of a hydro(halo)fluoroalkane includes a hydrofluoroalkane, i.e., an alkane in which at least one but not all of the hydrogen atoms have been replaced by fluorine.

Unless otherwise stated, as used herein, any reference to a ($C_{3-6}$) (hydro)fluoroalkene, hydrofluoroalkane or hydro(halo)fluoroalkane refers to a (hydro)fluoroalkene, hydrofluoroalkane or hydro(halo)fluoroalkane having from 3 to 6 carbon atoms, i.e. hydro(halo)fluoro-propane, butane, pentane or hexane or a (hydro)fluoro-propene, butene, pentene or hexene.

The (hydro)fluoroalkenes produced by the process of the invention contain a double bond and may thus exist as E (entgegen) and Z (zusammen) geometric isomers about each individual double bond. All such isomers and mixtures thereof are included within the scope of the invention.

Unless otherwise stated, as used herein, by the term "dehydrohalogenation" (or dehydrohalogenating), we refer to the removal of hydrogen halide (e.g. HF, HCl, HBr or HI), for example from a hydro(halo)fluoroalkane. Thus the term "dehydrohalogenation" includes "dehydrofluorination", "dehydrochlorination", "dehydrobromination" and "dehydroiodination" of a hydro(halo)fluoroalkane.

The present invention provides a process for preparing a compound of formula $CX_3(CX_2)_nCX=CX_2$ or $CX_3CX=CX(CX_2)_nCX_3$ wherein each X is, independently, H or F provided that at least one X is F and n is 0, 1, 2 or 3, which process comprises dehydrohalogenating a compound of formula $CX_3(CX_2)_nCXYCHX_2$ or $CX_3(CX_2)_nCXHCYX_2$ or $CX_3CXHCXY(CX_2)_nCX_3$ or $CX_3CXYCXH(CX_2)_nCX_3$ wherein each X is, independently, H or F provided that at least one X is F, n is 0, 1, 2 or 3 and Y is F, Cl, Br, or I, in the presence of a zinc/chromia catalyst.

In some embodiments, a preferred feed for the process of the invention is a mixed fluoro-chlorohexahalopropane or a hexafluoropropane.

Preferably, the compound of formula $CX_3(CX_2)_nCX=CX_2$ is $CF_3(CX_2)_nCF=CX_2$. This compound may be prepared by dehydrohalogenating a compound of formula $CF_3(CX_2)_nCFYCHX_2$ or $CF_3(CX_2)_nCFHCYX_2$.

More preferably, the compound of formula $CX_3CX=CX(CX_2)_nCX_3$ is $CF_3CF=CH(CX_2)_nCX_3$. This compound may be prepared by dehydrohalogenating a compound of formula $CF_3CFHCHY(CX_2)_nCX_3$ or $CX_3CFYCH_2(CX_2)_nCX_3$.

Preferably, n=0. The process is particularly suitable for preparing 2,3,3,3-tetrafluoropropene ($CF_3CF=CH_2$, HFC-1234yf) or 1,2,3,3,3-pentafluoropropene ($CF_3CF=CHF$, HFC-1225ye). In a particularly preferred embodiment, the invention may be used for preparing HFC-1225ye from either HFC-236ea or HFC-236cb, especially HFC-236ea.

$CF_3CF=CH_2$ and 1,3,3,3-tetrafluoropropene ($CF_3CH=CHF$) may be together prepared by the process of the invention. Alternatively, $CF_3CF=CH_2$ and 1,2,3,3,3-pentafluoropropene ($CF_3CF=CHF$) may be together prepared by the process of the invention.

$CF_3CF=CH_2$ may be prepared by dehydrohalogenating a compound of formula $CF_3CFYCH_3$ or $CF_3CFHCYH_2$.

The process of the invention is suitable for preparing any $C_{3-6}$ (hydro)fluoroalkene by dehydrohalogenating (e.g. dehydrofluorinating or dehydrochlorinating) a $C_{3-6}$ hydro(halo)fluoroalkane. Optionally, the $C_{3-6}$ hydro(halo)fluoroalkane may first be fluorinated to a $C_{3-6}$ hydrofluoroalkane which may then be dehydrofluorinated to a $C_{3-6}$ (hydro)fluoroalkene.

Preferably, the $C_{3-6}$ (hydro)fluoroalkene is a (hydro)fluoropropene prepared by the dehydrohalogenation of a hydro(halo)fluoropropane. By way of example and for simplicity, unless otherwise stated, the remainder of the specification will describe the process of the invention with reference to the preparation of (hydro)fluoropropenes. The skilled person will understand that such discussion is equally applicable to the preparation of (hydro)fluoro-butenes, pentenes and hexenes.

(Hydro)fluoropropenes prepared by the process of the invention may contain 0, 1, 2, 3, 4 or 5 hydrogen atoms and 1, 2, 3, 4, 5 or 6 fluorine atoms. Preferred (hydro)fluoropropenes are those having from 3 to 5 fluorine atoms (and thus from 1 to 3 hydrogen atoms), particularly 4 or 5 fluorine atoms (and thus 1 or 2 hydrogen atoms). In other words, preferred (hydro)fluoropropenes are tetrafluoropropenes and pentafluoropropenes.

Examples of suitable tetrafluoropropenes include 2,3,3,3-tetrafluoropropene ($H_2C=CFCF_3$), 1,3,3,3-tetrafluoropropene (HFC=CHCF$_3$), 1,2,3,3-tetrafluoropropene (HFC=CFCF$_2$H), 1,1,3,3-tetrafluoropropene ($F_2C=CHCF_2H$) and 1,1,2,3-tetrafluoropropene ($F_2C=CFCH_2F$). 1,3,3,3-tetrafluoropropene and 2,3,3,3-tetrafluoropropene ($H_2C=CFCF_3$) are preferred tetrafluoropropenes, 2,3,3,3-tetrafluoropropene being particularly preferred. Unless otherwise stated, this 2,3,3,3-tetrafluoropropene will be referred to hereinafter as HFC-1234yf and 1,3,3,3-tetrafluoropropene will be referred to as HFC-1234ze.

Examples of suitable pentafluoropropenes include 1,2,3,3,3-pentafluoropropene (HFC=CFCF$_3$), 1,1,3,3,3-pentafluoropropene ($F_2C=CHCF_3$) and 1,1,2,3,3-pentafluoropropene ($F_2C=CFCF_2H$). Of these, 1,2,3,3,3-pentafluoropropene (HFC=CFCF$_3$) is preferred.

The (hydro)fluoropropenes which can be made by the process of the invention may be prepared starting from one or more of a large number of hydro(halo)fluoropropanes. Again, by way of example and for simplicity, unless otherwise stated, the remainder of the specification will be described with reference to the preparation of HFC-1234yf.

HFC-1234yf may be prepared by a process comprising the dehydrofluorination of 1,1,1,2,2-pentafluoropropane ($CH_3CF_2CF_3$) or 1,1,1,2,3-pentafluoropropane ($CH_2FCHFCF_3$). 1,1,1,2,2-pentafluoropropane, for example, may be prepared by fluorinating one or more of a large number of hydrochlorofluoropropanes including tetrafluorochloropropanes such as 1,1,1,2-tetrafluoro-2-chloropropane and 1,1,2,2-tetrafluoro-1-chloropropane, trifluorodichloropropanes such as 1,1,1-trifluoro-2,2-dichloropropane, 1,1,2-trifluoro-1,2-dichloropropane and 1,2,2-trifluoro-1,1-dichloropropane, difluorotrichloropropanes such as 2,2-difluoro-1,1,1-trichloropropane, 1,2-difluoro-1,1,2-trichloropropane and 1,1-difluoro-1,2,2-trichloropropane and fluorotetrachloropropanes such as 1-fluoro-1,1,2,2-tetrachloropropane and 2-fluoro-1,1,1,2-tetrachloropropane. 1,1,1,2,2-pentafluoropropane (and thus ultimately HFC-1234yf) may also be prepared starting from 1,1,1,2,2-pentachloropropane. In any of the above hydrohalo(fluoro)propane precursors to 1,1,1,2,2-pentafluoropropane, one or more of the chlorine substituents may be replaced by bromine or iodine.

Preferred hydro(halo)fluoropropanes for preparing HFC-1234yf include 1,1,1,2,2-pentafluoropropane, 1,1,1,2-tetrafluoro-2-chloropropane and 1,1,1-trifluoro-2,2-dichloropropane. It will be understood by the skilled person that 1,1,1-trifluoro-2,2-dichloropropane may be fluorinated to give 1,1,1,2-tetrafluoro-2-chloropropane and/or 1,1,1,2,2-pentafluoropropane. 1,1,1,2-tetrafluoro-2-chloropropane may also be fluorinated to produce 1,1,1,2,2-pentafluoropropane, which may then be dehydrofluorinated to give HFC-1234yf.

Alternatively, 1,1,1,2-tetrafluoro-2-chloropropane may be dehydrochlorinated to give HFC-1234yf.

In a preferred aspect of the invention, it may be found that the process of the invention may be utilised to effect a degree of isomerisation of the (hydro) fluoroalkene of the invention. More specifically, and particularly when the (hydro) fluoroalkene is R-1225ye, the effect of the resultant (hydro) fluoroalkene being in contact with the catalyst of the invention may be to alter the ratio of E to Z isomers, thereby causing isomerisation.

In the particular context of R-1225ye, the effect is to increase the ratio of Z isomer to the E isomer.

In a further aspect of the invention, there is provide a process for isomerising a $C_{3-6}$ (hydrohalo) fluoroalkene by contacting the $C_{3-6}$ (hydrohalo) fluoroalkene with a catalyst. Also provided is the use of a catalyst for isomerising a $C_{3-6}$ (hydrohalo) fluoroalkene.

In a further aspect, there is provided a process for isomerising a $C_{3-6}$ (hydrohalo)fluoroalkene, the process comprising (i) contacting a E-$C_{3-6}$ (hydrohalo)fluoroalkene with a catalyst to convert the E-$C_{3-6}$ (hydrohalo) fluoroalkene to the $C_{3-6}$ Z-(hydrohalo)fluoroalkene. Conveniently, the $C_{3-6}$ Z-(hydrohalo)fluoroalkene can be recovered, and e.g. used in a subsequent procedure.

In a further aspect, the subject invention provides the use of a catalyst for isomerising a $C_{3-6}$ (hydrohalo)fluoroalkene, the use comprising (i) contacting a E-$C_{3-6}$ (hydrohalo)fluoroalkene with a catalyst to convert the E-$C_{3-6}$ (hydrohalo)fluoroalkene to the Z—$C_{3-6}$ (hydrohalo)fluoroalkene. Conveniently, the I—$C_{3-6}$ (hydrohalo)fluoroalkene can be recovered, and e.g. used in a subsequent procedure.

By "isomerisation" in this context is preferably meant changing the ratio of the E and Z isomers (e.g. increasing the level of Z isomer) from what it was previously or, in particular in a situation where the isomerisation is carried out in situ, for instance as part of a preparation step for the (hydrohalo) fluoroalkene, changing the ratio of E and Z isomers (e.g. increasing the level of Z isomer) compared to what it would have been if the catalyst had not been utilised.

In a further aspect, the invention also provides an isomer blend produced according to a process of the invention. The invention also provides a refrigerant comprising an isomer blend produced according to the process of the invention, and an automobile having an air conditioning system utilizing such an isomer blend.

Conveniently in an aspect of the invention, the invention may work by changing the E/Z isomer ratio from that which is the kinematic determined mixture of isomers, from the reaction preparing the (hydrohalo) fluoroalkene.

In a further aspect of the invention, there is provided a process for making a $C_{3-6}$ (hydrohalo) fluoroalkene composition comprising an enhanced level of Z isomer, conveniently a level of Z isomer enhanced beyond the level present when the $C_{3-6}$ (hydrohalo) fluoroalkene was formed, or the kinematic determined level of the Z isomer of the (hydrohalo) fluoroalkene, comprising the step of using a catalyst. Conveniently this aspect of the invention may comprise a clean up step which enhances the level of Z isomer in such a composition.

In utilities where it is preferable to increase the level of the Z isomer in the blend, it is possible using the method of the invention to increase the level of Z isomer by isomerising E isomer present in the blend to the Z isomer. The limit of how much E isomer can be converted to Z isomer is determined by thermodynamic considerations.

The reaction pathways described above for producing HFC-1234-yf from 1,1,1,2,2-pentafluoropropane, 1,1,1,2-tetrafluoro-2-chloropropane and 1,1,1-trifluoro-2,2-dichloropropane are illustrated below.

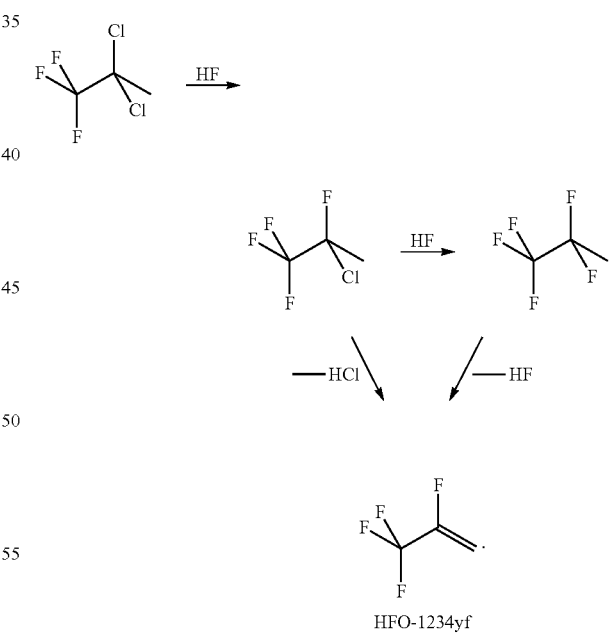

In a further embodiment, HFC-1234yf may be prepared starting from 1,1,1-trifluoro-2,3-dichloropropane, which can readily be prepared by chlorinating 1,1,1-trifluoromethylpropene. It is believed that there are two principal routes to HFC-1234yf from 1,1,1-trifluoro-2,3-dichloropropane, as illustrated below.

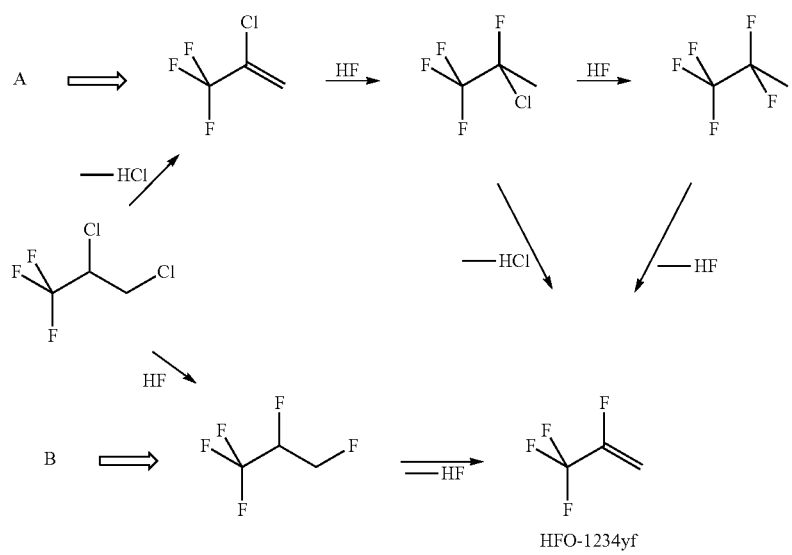

Route B proceeds via the fluorination (e.g. using HF, optionally in the presence of a chromia-containing catalyst) of 1,1,1-trifluoro-2,3-dichloropropane to give 1,1,1,2,3-pentafluoropropane which is then dehydrofluorinated to give HFC-1234yf. However, it is believed that route A may be favoured over route B.

Route A proceeds by dehydrochlorination of 1,1,1-trifluoro-2,3-dichloropropane to give 3,3,3-trifluoro-2-chloropropene which is then hydrofluorinated to give 1,1,1,2-tetrafluoro-2-chloropropane. These two steps may be carried out in one pot by contacting 1,1,1-trifluoro-2,3-dichloropropane with HF in the presence of a catalyst. However, it is believed that a two-stage reaction zone may be preferred, the first zone employing a relatively low HF:organics ratio (e.g. from about 1:1 to about 5:1) to promote the dehydrochlorination and the second zone employing a relatively high HF:organics ratio (e.g. from about 5:1 to about 30:1) to promote the hydrofluorination. As described above, 1,1,1,2-tetrafluoro-2-chloropropane may be fluorinated to produce 1,1,1,2,2-pentafluoropropane (e.g. using HF, optionally in the presence of a chromia-containing catalyst), which may then be dehydrofluorinated to give HFC-1234yf. Alternatively, 1,1,1,2-tetrafluoro-2-chloropropane may be directly dehydrochlorinated to give HFC-1234yf.

1,1,1-trifluoro-2,3-dichloropropane is commercially available, but may also be prepared via a synthetic route starting from the cheap feedstocks carbon tetrachloride (CCl$_4$) and ethylene. These two starting materials may be telomerised to produce 1,1,1,3-tetrachloropropane, which may then be fluorinated to produce 1,1,1,3-tetrafluoropropane (e.g. using HF, optionally in the presence of a chromia-containing catalyst). Dehydrofluorination of 1,1,1,3-tetrafluoropropane (e.g. using NaOH) would then produce 3,3,3-trifluoropropene, which may then be readily chlorinated (e.g. with chlorine) to produce 1,1,1-trifluoro-2,3-dichloropropane. This reaction scheme is summarised below.

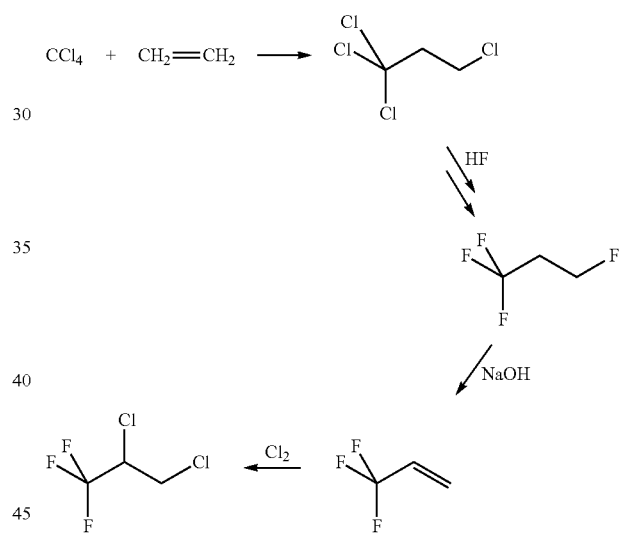

As mentioned above, 1,1,1,2,2-pentafluoropropane may be prepared starting from 1,1,1,2,2-pentachloropropane. In this route (see below), 1,1,1,2,2-pentachloropropane is fluorinated (e.g. using HF, optionally in the presence of a chromia-containing catalyst) to produce 1,1,1,2-tetrafluoro-2-chloropropane, which may also be fluorinated to produce 1,1,1,2,2-pentafluoropropane followed by dehydrofluorination to give HFC-1234yf. Alternatively, 1,1,1,2-tetrafluoro-2-chloropropane may be directly dehydrochlorinated to give HFC-1234yf.

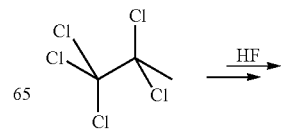

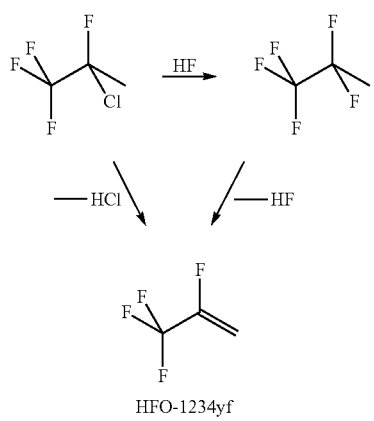

HFO-1234yf 1,1,1,2,2-pentachloropropane is a convenient intermediate in a route to HFC-1234yf starting from acetone. In such a synthetic route, acetone may be chlorinated (for example using chlorine over a chromia catalyst) to produce 1,1,1-trichloroacetone, which may be further chlorinated (for example using $PCl_5$—see Advanced Organic Chemistry (Ed M B Smith and J March), Fifth Edition, page 1195) to produce 1,1,1,2,2-pentachloropropane, as illustrated below.

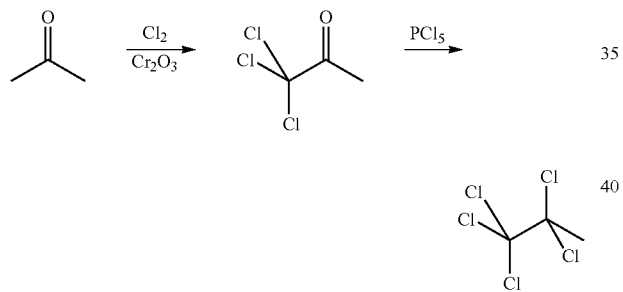

Within the broad ambit of the invention, it has been found that the preferred conditions for dehydrofluorination may depend on a number of variables, including the exact nature of the catalyst, and the pressure at which the reaction is carried out.

For instance, it has been found that the rate of fouling of the catalyst may be a function of the catalyst formulation. In general, the lower the level of zinc which was incorporated into the catalyst, the more resistant the catalyst was to fouling; chromia catalyst containing no zinc was more resistant to fouling than chromia catalysts containing some zinc. Further, when the process was carried out at atmospheric pressure, chromia catalysts were generally more resistant to fouling than zinc/chromia catalysts.

However, chromia catalysts containing no zinc at all were more susceptible to crystallisation under commercial production conditions. On a small scale, chromia catalysts of the type used in the examples were found to be stable in an inert atmosphere to temperatures around 440° C., but this temperature was lower in oxidising atmospheres. It was considered that it was likely that chromia containing no zinc would crystallise at operational temperatures, or at least during catalyst regenerations. Crystallisation is highly exothermic, and very problematic in industrial scale production.

Additionally, high levels of conversion of 1,1,1,2,3,3-hexafluoropropene (HFC-236ea) to 1,2,3,3,3-pentafluoropropene (HFC-1225ye) were observed when the reaction was carried out at greater than about 300° C.

When the process is carried out at super-atmospheric pressure, different criteria apply. It was observed that at pressure, conversion rates of HFC-236ea to HFC-1225ye were higher if the reaction were carried out in the absence of an added HF flow. It was not possible to remove all HF from the reaction since HF is generated where HFC-236ea is dehydrofluorinated. However, a reduction in the HF level in the reactant stream resulted in higher conversion of HFC-236ea to HFC-1225ye, suggesting that (at least at pressure) the conversion is inhibited by HF. Further and surprisingly, if HF levels were reduced or removed from the reactant stream, the level of fouling observed on the catalyst was surprisingly low. Operating the process of the invention at super atmospheric pressure may be desirable for various scale-up and general processing reasons, allowing for example greater productivity from apparatus of a given volume run at pressure.

The invention will now be illustrated, but not limited, by the following Examples.

EXAMPLE 1

Dehydrofluorination of 1,1,1-trifluoro-2,3-dichloropropane

A 2 g sample of an amorphous catalyst composed of 6% Zn by weight on chromia was charged to a 15 cm×1.25 mm Inconnel reaction tube installed inside a tubular furnace. This catalyst was dried at 250° C. for 1 hour then pre-fluorinated at an $N_2$:HF ratio of 6:1 for 1 hour at 250° C. before increasing the temperature to 380° C. at which point the nitrogen diluent flow was stopped. After approximately 18 hours, the HF feed was switched off and the reactor was cooled to 200° C.

The organic feed (comprising 1,1,1-trifluoro-2,3-dichloropropane) and HF were then passed over the catalyst with a contact time of 5 seconds at a reaction temperature of from 180 to 380° C. (varied at 20° C. intervals) and a pressure of 1 bara using either an HF:organics ratio of 15:1 or 5:1. At each temperature, the system was allowed to equilibrate for about 20 minutes before reactor off-gas samples were taken at each temperature for analysis by either GC or GC-MS. The reaction products could be resolved using a Plot Silica column with temperature programming (at about 40-200° C. at 5° C./min). The GC method was calibrated using the available standards (principally the feed and product) and an average of these was used to quantify those components identified but for which standards were not available and any unknowns.

Figure 2:
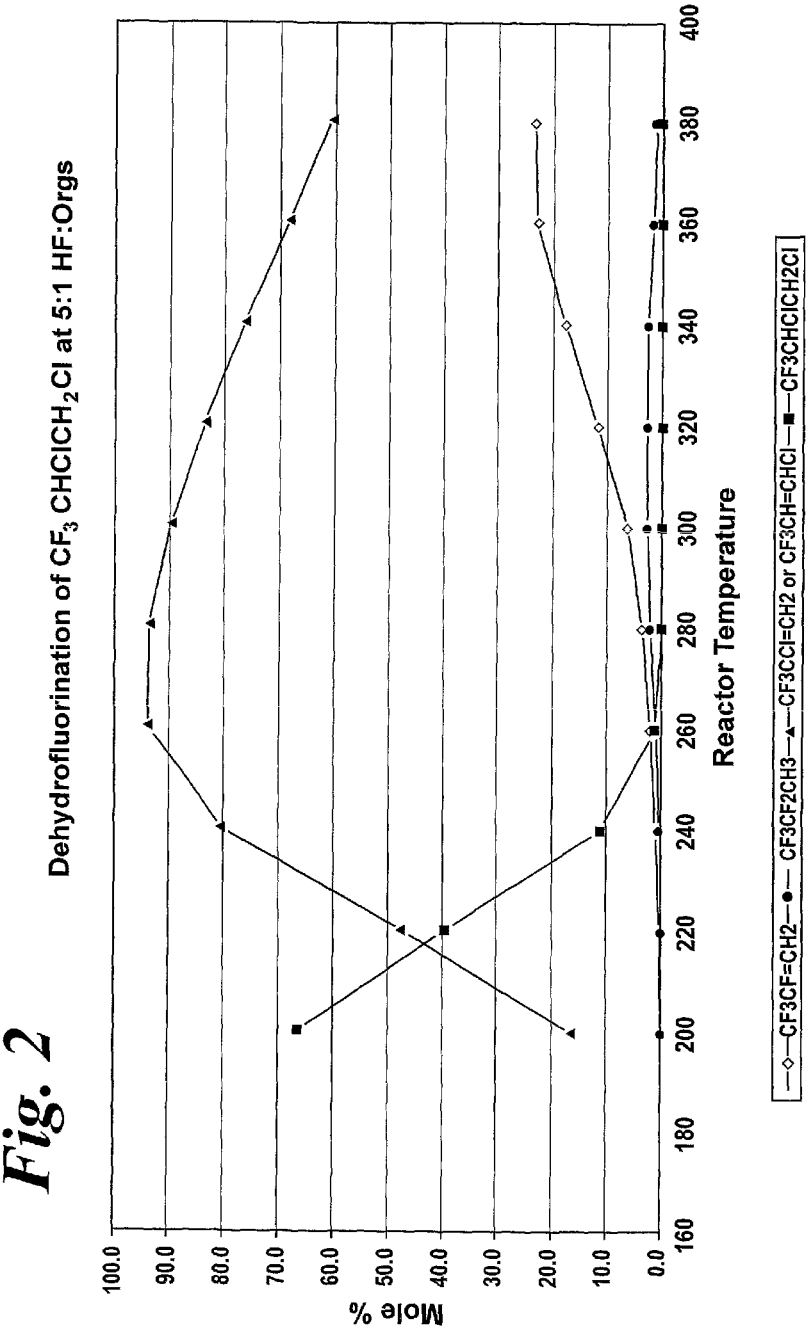
FIG. 2 is a graphical representation of the dehydrofluorination of CF3CClCH2Cl at a 5:1 HF to Organics ratio at various reactor temperatures.

The results of the temperature scans at the two different HF:organics ratios are presented in Tables 1 and 2 and FIGS. 1 and 2.

TABLE 1

Dehydrofluorination of $CF_3CHClCH_2Cl$ at an HF:organics ratio of 15:1

| Compound | Reaction temperature (° C.) | | | | | | | | | | |
|---|---|---|---|---|---|---|---|---|---|---|---|
| (mol %) | 180 | 200 | 220 | 240 | 260 | 280 | 300 | 320 | 340 | 360 | 380 |
| $CF_3CF=CH_2$ | 0.0 | 0.0 | 0.3 | 2.6 | 4.9 | 7.9 | 15.3 | 25.4 | 37.6 | 41.1 | 0.0 |
| $CF_3CF_2CH_3$ | 0.0 | 0.0 | 0.0 | 0.4 | 3.1 | 5.0 | 5.6 | 5.2 | 4.3 | 2.4 | 0.0 |
| $CF_3CCl=CH_2$ or $CF_3CH=CHCl$ | 4.0 | 13.3 | 41.1 | 79.1 | 90.3 | 85.9 | 78.1 | 67.7 | 53.8 | 42.5 | 4.0 |
| Unknown | 0.4 | 2.8 | 9.4 | 7.2 | 0.2 | 0.0 | 0.0 | 0.0 | 0.0 | 0.0 | 0.4 |
| Unknown | 16.8 | 22.0 | 10.3 | 1.6 | 0.0 | 0.0 | 0.0 | 0.0 | 0.0 | 0.0 | 16.8 |
| $CF_3CHClCH_2Cl$ | 78.4 | 61.1 | 36.5 | 6.6 | 0.2 | 0.1 | 0.0 | 0.0 | 0.0 | 0.0 | 78.4 |

TABLE 2

Dehydrofluorination of $CF_3CHClCH_2Cl$ at an HF:organics ratio of 5:1

| Compound | Reaction temperature (° C.) | | | | | | | | | | |
|---|---|---|---|---|---|---|---|---|---|---|---|
| (mol %) | 180 | 200 | 220 | 240 | 260 | 280 | 300 | 320 | 340 | 360 | 380 |
| $CF_3CF=CH_2$ | — | 0.0 | 0.2 | 1.0 | 2.1 | 3.4 | 6.2 | 11.7 | 17.7 | 23.1 | 23.4 |
| $CF_3CF_2CH_3$ | — | 0.0 | 0.0 | 0.2 | 0.8 | 2.0 | 2.6 | 2.8 | 2.5 | 1.5 | 1.1 |
| $CF_3CCl=CH_2$ or $CF_3CH=CHCl$ | — | 16.4 | 47.7 | 80.6 | 93.8 | 93.5 | 89.8 | 83.6 | 76.3 | 68.3 | 60.7 |
| Unknown | — | 2.0 | 5.5 | 4.5 | 0.8 | 0.1 | 0.0 | 0.0 | 0.0 | 0.0 | 0.0 |
| Unknown | — | 14.3 | 5.4 | 1.1 | 0.1 | 0.0 | 0.0 | 0.0 | 0.0 | 0.0 | 0.0 |
| $CF_3CHClCH_2Cl$ | — | 66.6 | 39.6 | 10.9 | 1.2 | 0.0 | 0.0 | 0.0 | 0.0 | 0.0 | 0.0 |

Turning first to the data obtained using the HF:organics ratio of 15:1 (Table 1 and FIG. 1), the feed level of $CF_3CHClCH_2Cl$ dropped fairly rapidly as the temperature increased and conversion appeared complete around 280° C. As the feed level dropped the species identified as $CF_3CCl=CH_2$ increased, indicating it to be the primary reaction product, formed by elimination of HCl. It is believed that the next step was hydrofluorination of $CF_3CCl=CH_2$ to give $CF_3CFClCH_3$. HFC-1234yf could be formed from $CF_3CFClCH_3$ directly by dehydrochlorination or indirectly via fluorination to give $CF_3CF_2CH_3$ followed by dehydrofluorination.

This reaction mechanism requires both addition and elimination of hydrogen halides and therefore the outcome is likely to be very sensitive to HF:organics ratio. The experiments at lower ratio demonstrated this to be the case.

Regarding the data obtained using the HF:organics ratio of 5:1 (Table 2 and FIG. 2), complete conversion of the feed and peak concentration of $CF_3CCl=CH_2$ was observed at 260° C. and the final yields of HFC-1234yf were lower compared to the experiment with the higher HF:organics ratio. Without being bound by theory, it is believed that the onward reaction of $CF_3CCl=CH_2$, necessary to form the desired product, is favoured at higher HF:organics ratios but its initial formation is favoured at lower HF:organics ratios, indicating that a two-stage reaction zone might be preferred.

EXAMPLE 2

Dehydrofluorination of 1,1,1,2,2-pentafluoropropane

A 2 g sample of an amorphous catalyst composed of 6% Zn by weight on chromia was charged to a 15 cm×1.25 mm Inconel reaction tube installed inside a tubular furnace. This catalyst was dried at 250° C. for 1 hour then pre-fluorinated at an $N_2$:HF ratio of 6:1 for 1 hour at 250° C. before increasing the temperature to 380° C. at which point the nitrogen diluent flow was stopped. After approximately 18 hours, the HF feed was switched off and the reactor was cooled to 200° C.

Figure 3:
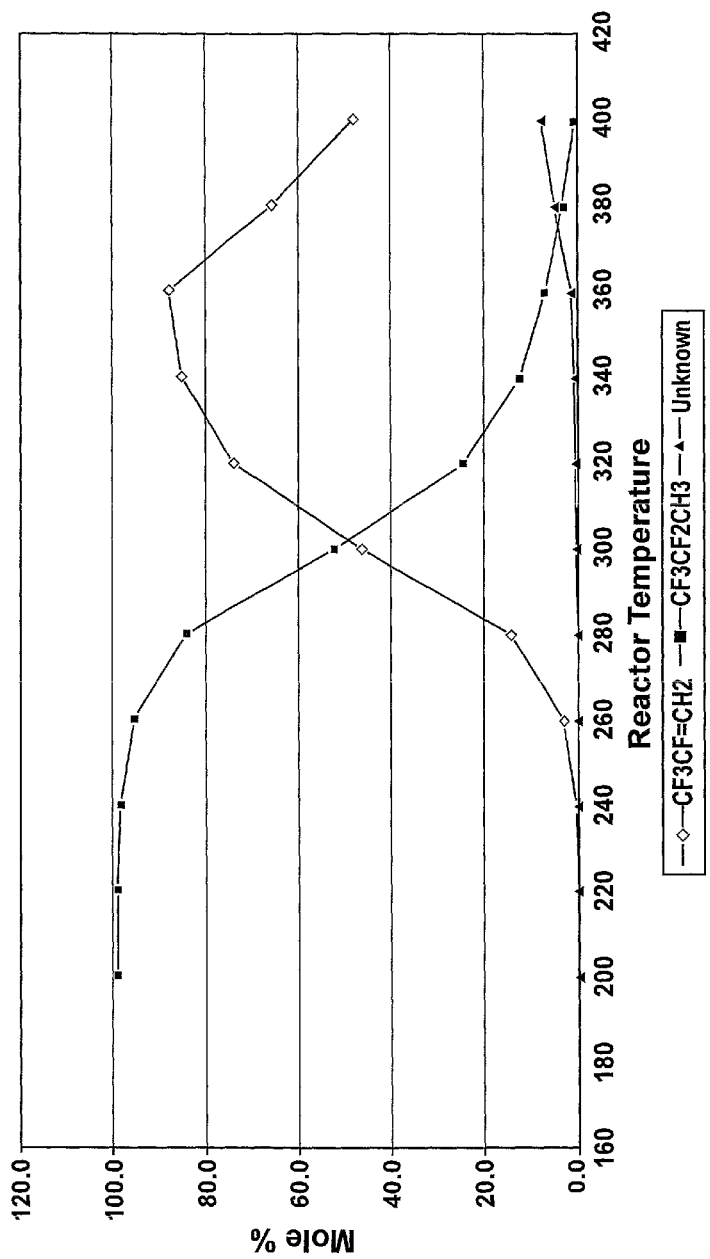
FIG. 3 is a graphical representation of the dehydrofluorination of CF3CF2CH3 Cl at a 5:1 HF to Organics ratio at various reactor temperatures.

The organic feed (comprising 1,1,1,2,2-pentafluoropropane) and HF was then passed over the catalyst with a contact time of 5 seconds at a reaction temperature of from 180 to 380° C. (varied at 20° C. intervals) and a pressure of 1 bara using either an HF:organics ratio of 15:1 or 5:1. At each temperature, the system was allowed to equilibrate for about 20 minutes before reactor off-gas samples were taken at each temperature for analysis by either GC or GC-MS as described above for Example 1 and the results are illustrated in Table 3 and FIG. 3. These results show that 1,1,1,2,2-pentafluoropropane was dehydrofluorinated to HFC-1234yf at high selectivity at about 300° C.

TABLE 3

Dehydrofluorination of $CF_3CF_2CH_3$ at and HF:organics ratio of 5:1

| Compound | Reaction temperature (° C.) | | | | | | | | | | |
|---|---|---|---|---|---|---|---|---|---|---|---|
| (mol %) | 200 | 220 | 240 | 260 | 280 | 300 | 320 | 340 | 360 | 380 | 400 |
| $CF_3CF=CH_2$ | 0.1 | 0.6 | 3.6 | 15.1 | 46.9 | 74.2 | 85.5 | 88.1 | 66.0 | 48.4 | 0.1 |
| $CF_3CF_2CH_3$ | 99.4 | 98.7 | 95.9 | 84.5 | 52.6 | 25.0 | 13.0 | 7.5 | 3.6 | 0.7 | 99.4 |
| Unknown | 0.1 | 0.2 | 0.3 | 0.4 | 0.4 | 0.7 | 0.9 | 1.5 | 5.2 | 8.2 | 0.1 |
| Unknown | 0.2 | 0.1 | 0.0 | 0.0 | 0.0 | 0.0 | 0.0 | 0.0 | 0.0 | 0.0 | 0.2 |

EXAMPLE 3

Dehydrofluorination of 1,1,1,2,2,3-hexafluoropropane (HFC-236cb) and 1,1,1,2,3,3-hexafluoropropane (HFC-236ea) with HF A 2 g sample of an amorphous catalyst composed of 6% Zn by weight on chromia was charged to a 15 cm×1.25 mm Inconel reaction tube installed inside a tubular furnace. This catalyst was dried at 250° C. for 1 hour then pre-fluorinated at an $N_2$:HF ratio of 6:1 for 1 hour at 250° C. before increasing the temperature to 380° C. at which point the nitrogen diluent flow was stopped. After approximately 18 hours, the HF feed was switched off and the reactor was cooled to 220-240° C.

Figure 4:
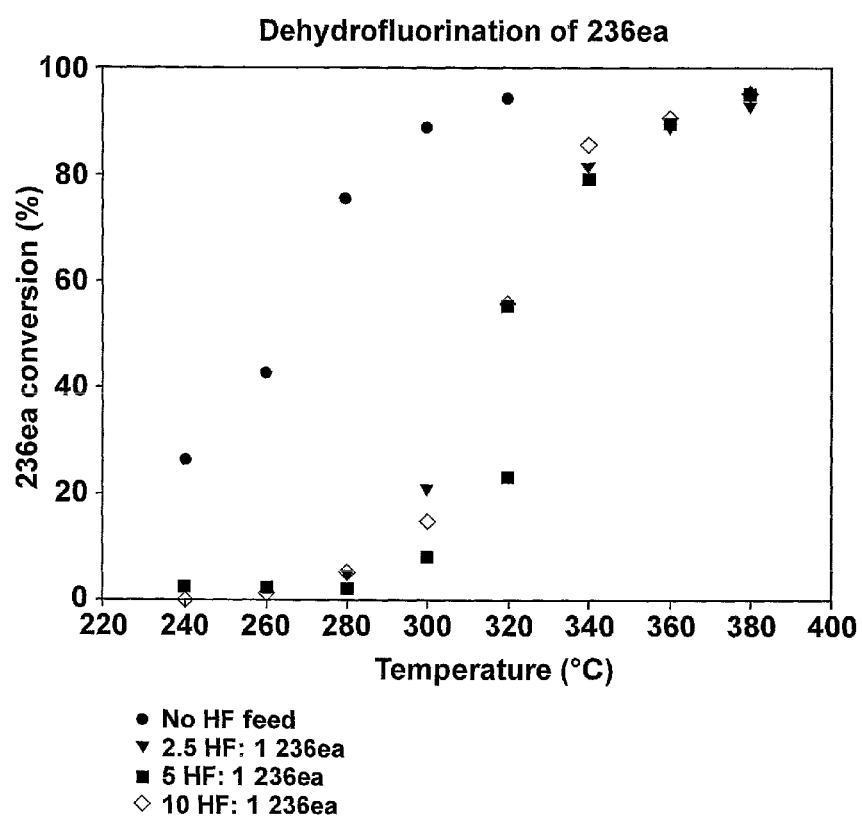
FIG. 4 is a graphical representation of the dehydrofluorination of 236ea at various temperatures and various feeds of HF.
Figure 5:
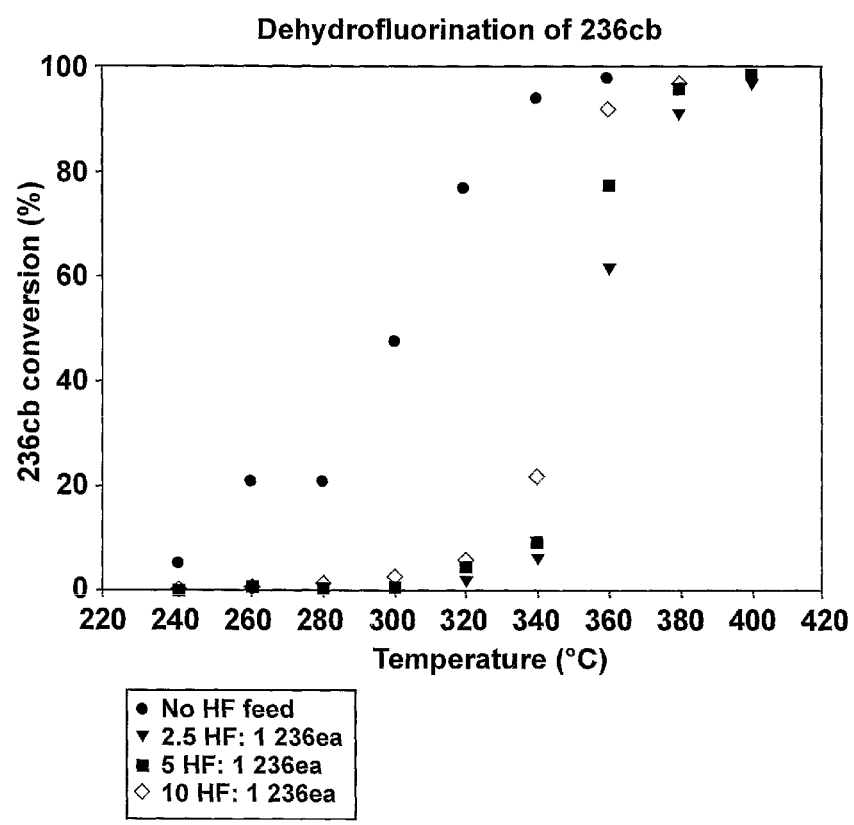
FIG. 5 is a graphical representation of the dehydrofluorination of 236cb at various temperatures and various feeds of HF.

Following pre-fluorination, the dehydrofluorination of either HFC-236ea or HFC-236cb was studied as a function of temperature and HF:236 ratio. Feed gas flow rates were chosen so that a contact time of c.a. 5 seconds was achieved between the catalyst and feed mixture. HF:236 ratios were explored in the range 0-10. At each temperature, the system was allowed to equilibrate for about 20 minutes before reactor off-gas samples were taken at each temperature for analysis by either GC or GC-MS as described above for Example 1 and the results are illustrated in Tables 4 and 5 and FIGS. 4 and 5.

TABLE 4

Dehydrofluorination of HFC-236ea at varying HF:organics ratios

| Temperature (° C.) | Ratio HF:236ea | 236ea Conversion (%) | Z-1225ye (%) | E-1225ye (%) | Selectivity (Z + E %) |
|---|---|---|---|---|---|
| 240.0 | 0.0 | 26.5 | 24.0 | 2.2 | 99.1 |
| 260.0 | 0.0 | 42.9 | 38.2 | 4.2 | 98.8 |
| 280.0 | 0.0 | 75.8 | 65.9 | 7.9 | 97.4 |
| 300.0 | 0.0 | 89.3 | 77.0 | 10.3 | 97.7 |
| 320.0 | 0.0 | 94.7 | 80.2 | 12.1 | 97.5 |
| 240.0 | 2.5 | 3.0 | 0.1 | 0.0 | 2.7 |
| 260.0 | 2.5 | 2.8 | 0.5 | 0.1 | 19.6 |
| 280.0 | 2.5 | 5.4 | 3.2 | 0.4 | 66.7 |
| 300.0 | 2.5 | 21.2 | 17.1 | 2.1 | 90.7 |
| 320.0 | 2.5 | 56.1 | 46.8 | 6.6 | 95.3 |
| 340.0 | 2.5 | 82.2 | 67.6 | 10.6 | 95.2 |
| 360.0 | 2.5 | 90.2 | 72.2 | 11.8 | 93.4 |
| 380.0 | 2.5 | 94.0 | 73.7 | 12.6 | 91.8 |
| 240.0 | 5.0 | 2.5 | 0.0 | 0.0 | 0.8 |
| 260.0 | 5.0 | 2.3 | 0.2 | 0.0 | 7.7 |
| 280.0 | 5.0 | 2.4 | 0.8 | 0.1 | 38.5 |
| 300.0 | 5.0 | 8.2 | 4.6 | 0.6 | 63.2 |
| 320.0 | 5.0 | 23.4 | 18.0 | 2.7 | 88.1 |
| 340.0 | 5.0 | 80.0 | 63.1 | 9.5 | 90.8 |
| 360.0 | 5.0 | 90.4 | 65.8 | 10.5 | 84.4 |
| 380.0 | 5.0 | 95.9 | 49.2 | 8.0 | 59.6 |
| 240.0 | 10.0 | 0.4 | 0.1 | 0.0 | 40.5 |
| 260.0 | 10.0 | 1.2 | 1.0 | 0.1 | 93.4 |
| 280.0 | 10.0 | 5.4 | 4.1 | 0.6 | 85.9 |
| 300.0 | 10.0 | 15.2 | 13.1 | 1.6 | 96.6 |
| 320.0 | 10.0 | 56.1 | 47.7 | 6.5 | 96.7 |
| 340.0 | 10.0 | 86.3 | 70.8 | 10.8 | 94.6 |
| 360.0 | 10.0 | 91.3 | 72.8 | 11.4 | 92.1 |
| 380.0 | 10.0 | 95.7 | 73.0 | 12.5 | 89.5 |

TABLE 5

Dehydrofluorination of HFC-236cb at varying HF:organics ratios

| Temperature (° C.) | Ratio HF:236cb | 236cb Conversion (%) | Z-1225ye (%) | E-1225ye (%) | Selectivity (Z + E %) |
|---|---|---|---|---|---|
| 240.0 | 0.0 | 5.0 | 3.8 | 0.4 | 83.2 |
| 260.0 | 0.0 | 20.6 | 16.2 | 2.2 | 89.7 |
| 280.0 | 0.0 | 20.6 | 17.4 | 2.1 | 94.3 |
| 300.0 | 0.0 | 47.3 | 39.5 | 5.1 | 94.3 |
| 320.0 | 0.0 | 76.7 | 63.4 | 9.1 | 94.6 |
| 340.0 | 0.0 | 93.6 | 77.4 | 11.2 | 94.6 |
| 360.0 | 0.0 | 97.6 | 78.5 | 12.3 | 93.0 |
| 240.0 | 2.5 | 0.3 | 0.0 | 0.0 | 0.0 |
| 260.0 | 2.5 | 0.3 | 0.0 | 0.0 | 4.8 |
| 280.0 | 2.5 | 0.3 | 0.1 | 0.0 | 23.8 |
| 300.0 | 2.5 | 0.6 | 0.4 | 0.0 | 69.7 |
| 320.0 | 2.5 | 1.8 | 1.3 | 0.2 | 82.8 |
| 340.0 | 2.5 | 6.1 | 4.5 | 0.7 | 84.7 |
| 360.0 | 2.5 | 61.6 | 46.2 | 7.3 | 86.9 |
| 380.0 | 2.5 | 90.8 | 69.0 | 11.8 | 88.9 |
| 400.0 | 5.0 | 96.7 | 70.2 | 12.8 | 85.8 |
| 240.0 | 5.0 | 0.0 | 0.0 | 0.0 | 0.0 |
| 260.0 | 5.0 | 0.4 | 0.0 | 0.0 | 0.0 |
| 280.0 | 5.0 | 0.2 | 0.1 | 0.0 | 54.2 |
| 300.0 | 5.0 | 0.5 | 0.4 | 0.1 | 81.5 |
| 320.0 | 5.0 | 4.5 | 1.5 | 0.3 | 39.3 |
| 340.0 | 5.0 | 9.0 | 6.2 | 1.0 | 79.7 |
| 360.0 | 5.0 | 77.4 | 55.9 | 9.0 | 83.8 |
| 380.0 | 5.0 | 95.6 | 67.1 | 11.3 | 81.9 |
| 400.0 | 5.0 | 98.2 | 61.2 | 10.9 | 73.4 |
| 240.0 | 10.0 | 0.3 | 0.0 | 0.0 | 7.1 |
| 260.0 | 10.0 | 0.3 | 0.1 | 0.0 | 26.5 |
| 280.0 | 10.0 | 0.8 | 0.4 | 0.1 | 55.6 |
| 300.0 | 10.0 | 2.3 | 1.3 | 0.2 | 61.7 |
| 320.0 | 10.0 | 5.7 | 4.1 | 0.6 | 84.1 |
| 340.0 | 10.0 | 21.6 | 14.8 | 2.4 | 79.2 |
| 360.0 | 10.0 | 91.6 | 64.3 | 10.9 | 82.2 |
| 380.0 | 10.0 | 96.2 | 59.8 | 10.2 | 72.8 |

The results show that both HFC-236ea and HFC-236cb can be used to prepare 3,3,3,2,1-pentafluoropropene (HFC-1225ye) by dehydrofluorination, but that HFC-236ea was generally more susceptible to dehydrofluorination than HFC-236cb under the conditions employed. The Z isomer of HFC-1225ye was predominantly formed, although significant quantities of the E isomer were also formed. The presence of HF strongly depresses the dehydrofluorination reaction.

EXAMPLE 4

In the ensuing Examples 4 to 6, the following general protocol applied.

A reactor tube was charged with 2 g catalyst, which was dried at 250° C. under nitrogen (65 ml/min) for 2 hours. The catalyst was then pre-fluorinated with HF (30 ml/min) and nitrogen (65 ml/min) for 1 hour at 250° C. The temperature was then ramped to 460° C. and the pre-fluorination continued under neat HF (30 ml/min) overnight. Feed rates and temperatures were then set so as to achieve the desired reactor conditions and the reactor off-gases sampled at an appropriate frequency using an automated system. HF was fed using a nitrogen sparge and so some dilution of the feed mixture with inerts was unavoidable.

When regeneration of the catalyst was necessary, the organic feed was switched off and the HF flow set to 6 ml/min and a mixture of air (3 ml/min) and nitrogen (60 ml/min) passed over the catalyst at 380° C. overnight.

In the Example itself, the reactor was charged with a 6% zinc/chromia catalyst. Following pre-fluorination the reactor was cooled to 340° C. and a reaction mixture consisting of HF (6 ml/min), HFC-236ea (1 ml/min) and nitrogen (5 ml/min) passed over it. Reactor off-gas (ROG) samples were regularly taken in order to monitor catalyst performance. When the catalyst performance was deemed to have dropped too far, the catalyst was regenerated as described above and the experiment repeated. A total of 3 such cycles were completed. HFC-1225ye Z yield data from these experiments is plotted in FIG. 6.

These experiments indicated that organic fouling of the catalyst occurred in use and was responsible for the observed loss in performance. Furthermore, the process could be completely reversed by an oxidative regeneration.

EXAMPLE 5

The following example demonstrates the impact of the HF:organic ratio on catalyst fouling rates.

The reactor was charged with a composite comprising a 6% zinc/chromia catalyst. In the first cycle following pre-fluorination the fouling rate was determined at an HF:HFC-236ea ratio of 3:1. In the second cycle following a standard regeneration the fouling rate was measured at a ratio of 6:1 and in the final cycle in this sequence it was re-measured at a ratio of 1.5:1. In these experiments the partial pressure of HF was constant at 0.5 bara and the contact time constant at 4.4 seconds. The Z-HFC-1225ye yield vs time for this sequence of experiments is plotted in FIG. 7. There did not appear to be any relationship between ratio and yield. At ratios between 3:1 and 6:1 the fouling rates appeared similar, but did look to increase at 1.5:1.

EXAMPLE 6

The following example demonstrates the impact of catalyst formulation on fouling rates and yield of HFC-1225ye.

Figure 8:
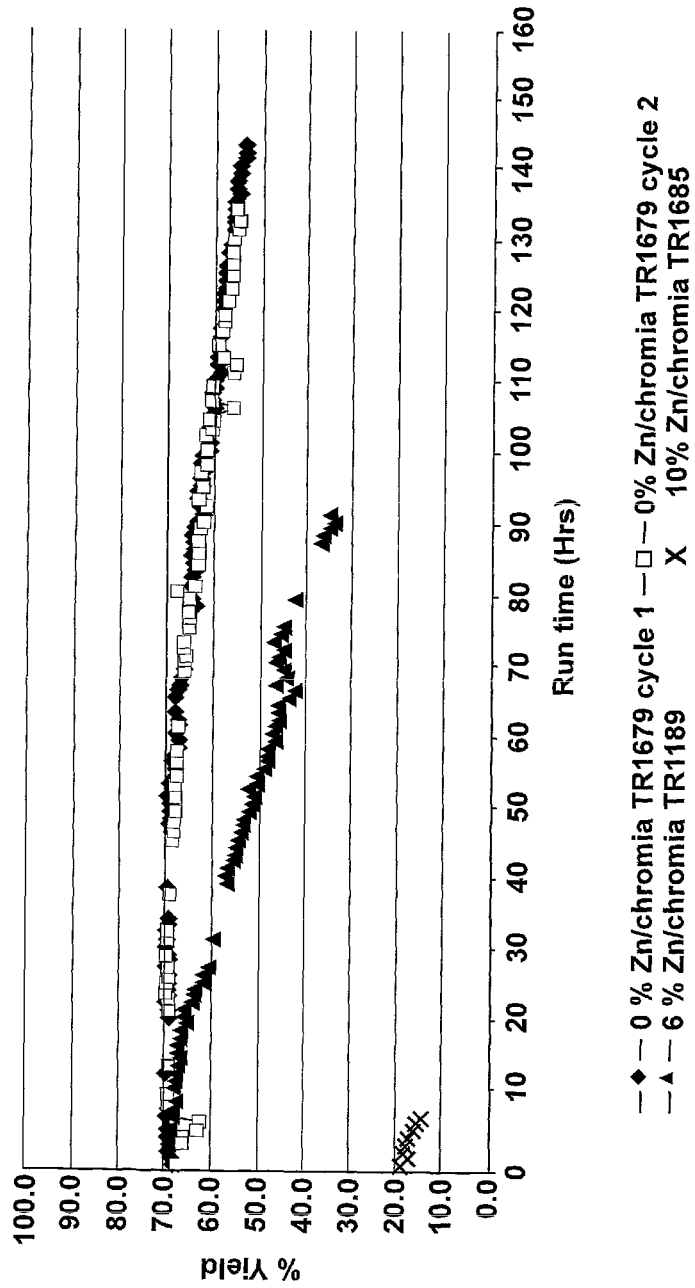
FIG. 8 is a graphical representation of the impact of various catalyst formulations on the yield of Z-1225ye and fouling rates using these formulations over various run times.

The relative performance of a 0% Zn/chromia, 6% Zn/chromia and 10% Zn chromia were determined using the methodology described above. The reaction temperature, ratio and contact times were all constant at 340° C., 6:1 and 4.4 seconds respectively over the sequence of experiments. The results are summarized in FIG. 8. The effect of Zn loading on performance and stability was quite marked. The initial performance of the 0% and 6% Zn catalysts was similar but the performance of the 10% catalyst was relatively poor. In terms of fouling rates it was also clear that the 0% Zn catalyst was the most stable.

EXAMPLE 7

Figure 9:
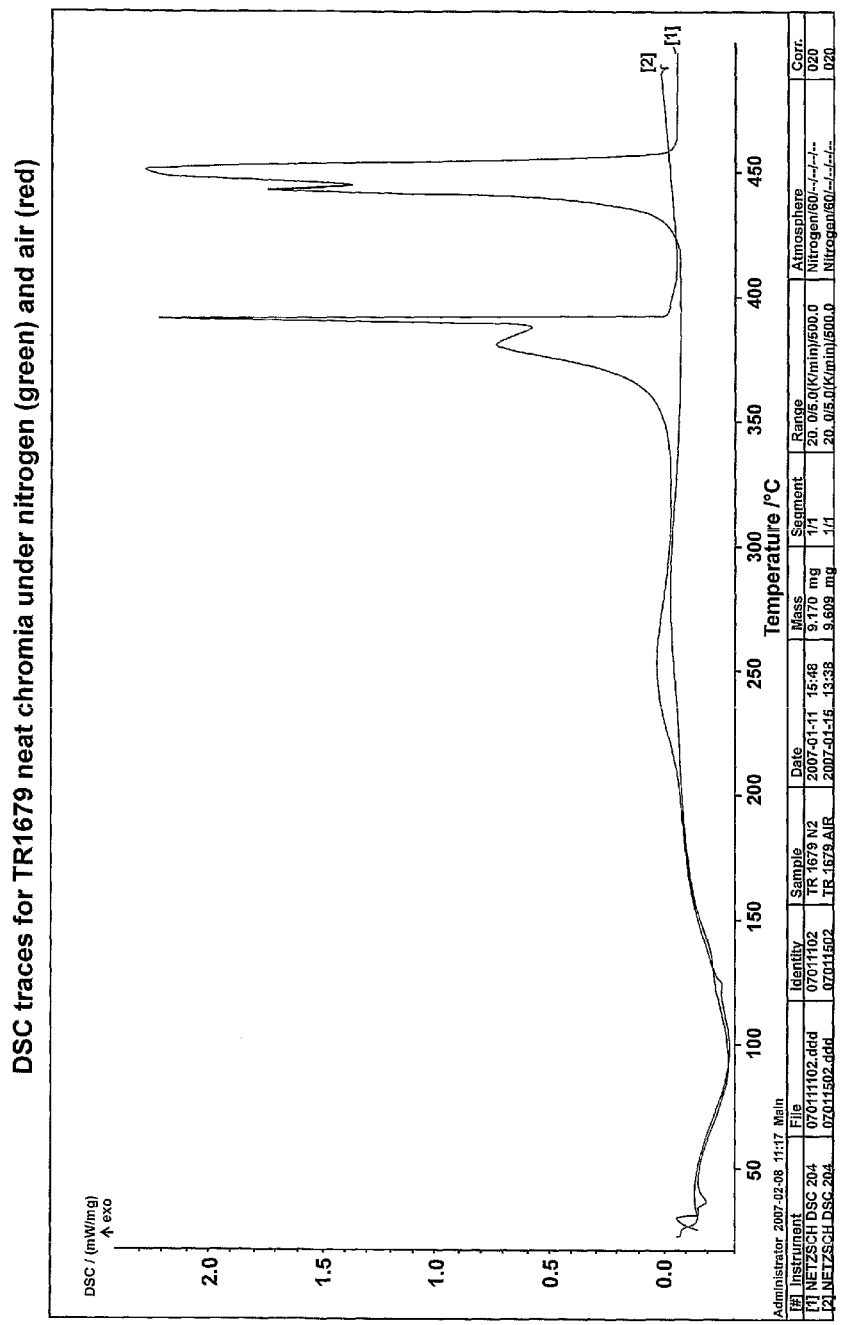
FIG. 9 depicts an analysis of a chromia catalyst containing no zinc using differential scanning calorimetry.

A sample of a chromia catalyst containing no zinc was analysed using differential scanning calorimentry (DSC) techniques under nitrogen and air atmospheres. The results are shown in FIG. 9.

The results show that in an inert atmosphere the chromia was stable to about 440° C., but that this was reduced under an oxidising atmosphere. From this it can be concluded that a chromia catalyst containing no zinc could crystallise in use, or at least during regenerations.

EXAMPLE 8

In a slight modification to Example 4, a reactor tube was prepared as outlined in the general protocol outlined in Example 4 and the feed rates were set at HF=6 ml/minute, HFC-236ea=2 ml/minute, nitrogen=4 ml/minute over a scan of temperature, on a series of different catalysts shown in Table 6. This example was conducted at atmospheric pressure.

TABLE 6

| | | | | | | | | | | | |
|---|---|---|---|---|---|---|---|---|---|---|---|
| Catalyst screening temperature scan results | | | | | | | | | | | |
| ° C. | 200 | 215 | 230 | 245 | 260 | 275 | 290 | 305 | 320 | 335 | 350 |
| Empty reactor tube | | | | | | | | | | | |
| HFD-1225ye yield | — | — | 0.7 | 0.3 | 0.2 | 0.2 | 0.1 | 0.1 | 0.2 | 0.2 | 0.3 |
| Pure chromia | | | | | | | | | | | |
| HFC-1225ye yield | 0.1 | 0.1 | 0.3 | 0.2 | 0.3 | 15.5 | 34.5 | 52.6 | 60.4 | 65.1 | 68.8 |
| 0.5% Zn/chromia | | | | | | | | | | | |
| HFC-1225ye yield | 0.0 | 0.1 | 0.3 | 0.4 | 0.4 | 9.9 | 30.1 | 51.5 | 61.0 | 66.0 | 69.3 |

TABLE 6-continued

Catalyst screening temperature scan results

6% Zn/chromia

| HFC-1225ye yield | 0.0 | 0.1 | 0.2 | 0.4 | 0.5 | 0.5 | 11.2 | 27.1 | 49.5 | 63.9 | 69.9 |

10% Zn/chromia

| HFC-1225ye yield | 0.0 | 0.0 | 0.1 | 0.3 | 0.5 | 4.5 | 15.4 | 31.5 | 49.6 | 61.1 | 68.9 |

| °C. | 365 | 380 | 395 | 410 | 425 | 440 | 455 | 470 | 485 | 500 |

Empty reactor tube

| HFD-1225ye yield | 0.5 | 0.8 | 1.2 | 1.8 | 2.2 | 2.6 | 2.8 | 2.8 | 2.9 | — |

Pure chromia

| HFC-1225ye yield | 71.2 | 73.9 | 73.9 | 73.2 | 73.3 | 74.2 | — | — | — | — |

0.5% Zn/chromia

| HFC-1225ye yield | 71.6 | 73.8 | 74.3 | 73.8 | 73.6 | — | — | — | — | — |

6% Zn/chromia

| HFC-1225ye yield | 72.7 | 74.0 | 74.3 | 74.7 | — | — | — | — | — | — |

10% Zn/chromia

| HFC-1225ye yield | 71.0 | 74.4 | 74.1 | 74.8 | 74.6 | — | — | — | — | — |

The results show that the conversion of HFC-236ea to HFC-1225ye is a catalytic one and not merely a thermal decomposition, based on the very poor yield obtained when using an empty tube.

Comparing yields between at between 260° C. and 305° C., chromia containing no zinc produces the highest conversion. At a temperature above 305° C., the conversion of all of catalysts tested is generally similar. It was also found that the fouling resistance decreased as the zinc loading increased. However, the apparent preferred performance of chromia catalysts containing no zinc should be balanced against the crystallisation tendency of pure chromia catalysts at scale.

EXAMPLE 9

In the ensuing experiments conducted at increased pressure the following general protocol applied.

Unless specified otherwise, the catalyst employed was a 6 wt % zinc/chromia catalyst which was charged to the rig. The catalyst was dried overnight in a stream of nitrogen (80 ml/min at 3 barg) and then prefluorinated in stages. In stage 1 the temperature was raised to 300° C. and the catalyst was contacted with dilute HF (4 ml/min+80 ml/min nitrogen at 3 barg). This treatment was continued overnight and then the nitrogen flow was switched off and the temperature maintained at 300° C. for a further 4 hours. After this period the temperature was ramped to 380° C. at 25° C./hr. These conditions were maintained for a further 7 hours. The HFC-236ea→HFC E/Z-1225ye reaction was then studied under a range of conditions.

In this example and Example 10, the conversion rate in the process of the invention when conducted at pressure is apparent, together with the benefit of omitting HF from the reactant flow.

Following pre-fluorination, the HF and HFC-236ea feed flows were set to approximately 90 and 30 m ml/min (at STP) respectively, and the impact of temperature on conversion studied at 5 barg and 10 barg. The results are summarized in FIG. 7.

TABLE 7

HFC-236ea→HFC-1225ye reaction at 3 HF:1 HFC-236ea

| Temperature (° C.) | Pressure (Barg) | HFC-236ea conversion (mol %) |
|---|---|---|
| 330 | 5 | 3.8079 |
| 350 | 5 | 3.7452 |
| 350 | 5 | 3.8359 |
| 370 | 5 | 3.8090 |
| 315 | 10 | 2.6044 |
| 330 | 10 | 5.1410 |
| 330 | 10 | 4.3250 |
| 350 | 10 | 8.6508 |
| 350 | 10 | 6.0846 |
| 330 | 5 | 3.5644 |
| 330 | 5 | 4.2492 |
| 350 | 5 | 3.9889 |
| 350 | 5 | 3.4571 |

Figure 10:
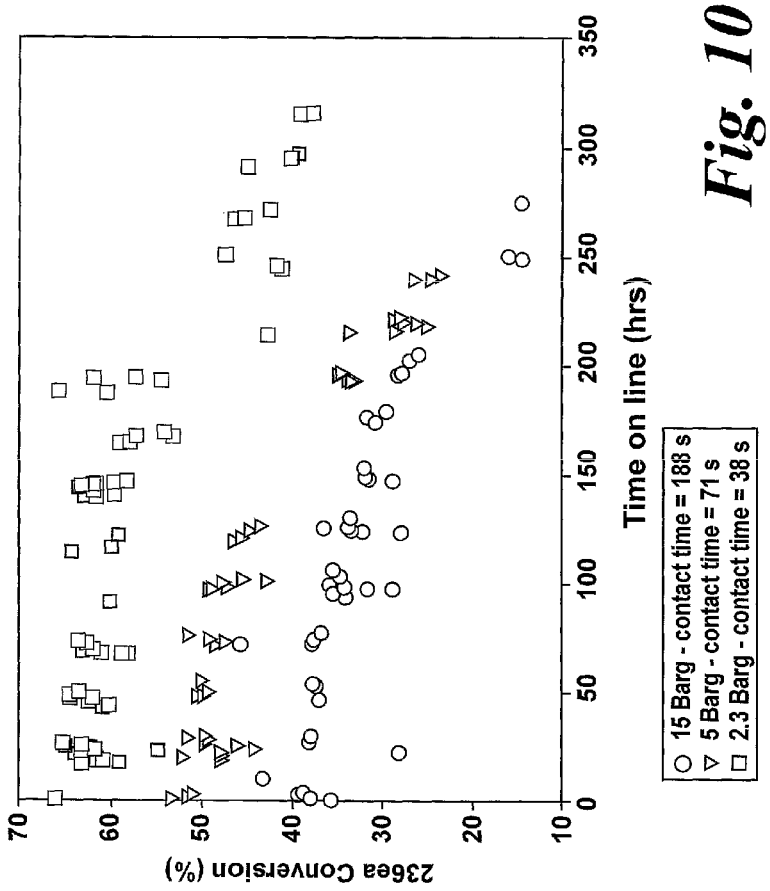
FIG. 10 provides a graphical representation of the conversion of R-236ea-R-1225ye over time, with coking as a function of pressure.
Figure 11:
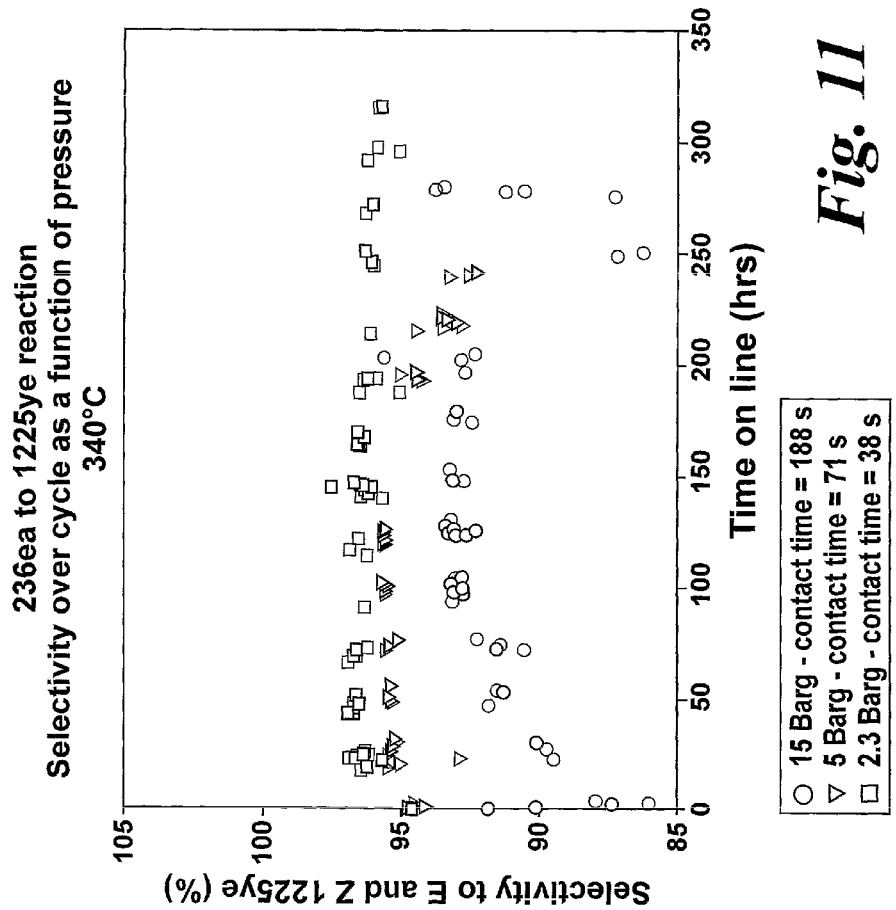
FIG. 11 provides a graphical representation of the conversion of R-236ea-R-1225ye over time, with selectivity over cycle as a function of pressure.

The catalyst was given an HF:air regeneration (15:1) at 380° C. and some of the data points at 5 barg operation repeated; these are also shown in FIG. 10.

EXAMPLE 10

Following on from Example 9, the experiment was repeated but with no co-fed HF. The resultant HFC-236ea conversion shown in Table 8.

TABLE 8

HFC-236ea→HFC-1225ye reaction without co-fed HF

| Temperature (° C.) | Pressure (Barg) | HFC-236ea conversion (mol %) |
|---|---|---|
| 330 | 5 | 46.7366 |
| 330 | 5 | 45.7122 |
| 340 | 5 | 52.8137 |
| 340 | 5 | 51.9489 |
| 340 | 5 | 52.0404 |
| 350 | 5 | 56.8593 |
| 350 | 5 | 57.5889 |

In the absence of HF there is a marked increase in catalyst performance, with higher conversion rates observed.

To further demonstrate the adverse effects that HF was causing, the feed was diluted with inert diluent nitrogen, with the effect measured in a single pass conversion at 340° C. The results are shown in Table 9.

TABLE 9

Impact of feed dilution on HFC-236ea→HFC-1225ye at 5 barg

| Temperature (° C.) | HFC-236ea feed (ml/min) | Nitrogen (ml/min) | Contact time (sec) | HFC-236ea mole fraction | HFC-236ea conversion (%) |
|---|---|---|---|---|---|
| 340 | 33.32 | 0 | 37.70 | 1.00 | 48.82 |
| 340 | 22.41 | 0 | 56.06 | 1.00 | 49.11 |
| 340 | 27.06 | 0 | 46.43 | 1.00 | 51.18 |
| 340 | 30.67 | 20 | 24.80 | 0.61 | 57.41 |
| 340 | 17.17 | 20 | 33.80 | 0.46 | 58.29 |
| 340 | 21.73 | 20 | 30.11 | 0.52 | 65.93 |
| 340 | 25.94 | 20 | 27.35 | 0.56 | 56.35 |
| 340 | 18.77 | 20 | 32.41 | 0.48 | 57.10 |
| 340 | 23.20 | 40 | 19.88 | 0.37 | 63.12 |
| 340 | 25.45 | 40 | 19.20 | 0.39 | 61.77 |
| 340 | 26.55 | 60 | 14.52 | 0.31 | 64.70 |
| 340 | 17.60 | 60 | 16.19 | 0.23 | 65.52 |
| 340 | 12.90 | 80 | 13.52 | 0.14 | 74.61 |
| 340 | 11.94 | 80 | 13.67 | 0.13 | 68.38 |

As the feed is diluted, the conversion rose even though the contact time is reducing.

EXAMPLE 11

This example demonstrates the lower than expected levels of catalyst fouling which were found to occur when the conversion of HFC-236ea to HFC-1226ye was carried out at pressure in the absence of HF. The catalyst was regenerated as described above in the context of Example 9 but substituting nitrogen for HF, and then "neat" HFC-236ea at a rate of approximately 20 ml/minute was passed over it at 340° C. and 5 barg. The catalyst performance was monitored, and the results are shown in Table 10.

TABLE 10

HFC-236ea→HFC-1225ye coking study at 340° C. and 5 barg in the absence of co-fed HF

| Time (hrs) | Temperature (° C.) | 236ea (ml/min) | CT (sec) | Normalised mole % | | | | | | | 236ee conversion (%) |
|---|---|---|---|---|---|---|---|---|---|---|---|
| | | | | 1234yf | 1225zc | Z-1225ye | E-1225ye | 227ea | 236cb | 236ee | |
| 0.0 | 340 | 2.89 | 435.44 | 0.15 | 0.00 | 57.60 | 7.49 | 1.37 | 7.07 | 26.17 | 73.83 |
| 0.3 | 340 | 26.92 | 46.67 | 0.19 | 0.00 | 43.86 | 5.96 | 0.41 | 4.35 | 45.01 | 54.99 |
| 1.8 | 340 | 19.75 | 63.61 | 0.20 | 0.00 | 43.84 | 5.97 | 0.27 | 3.70 | 45.83 | 54.17 |
| 2.6 | 340 | 28.23 | 44.51 | 0.20 | 0.00 | 43.69 | 5.94 | 0.26 | 3.82 | 45.92 | 54.08 |
| 3.6 | 340 | 22.67 | 55.42 | 0.21 | 0.00 | 43.73 | 5.94 | 0.25 | 3.97 | 45.77 | 54.23 |
| 4.4 | 340 | 22.77 | 55.17 | 0.20 | 0.00 | 43.91 | 6.02 | 0.22 | 3.42 | 46.10 | 53.90 |
| 5.0 | 340 | 27.46 | 45.76 | 0.21 | 0.00 | 44.05 | 6.01 | 0.22 | 3.31 | 46.08 | 53.92 |
| 21.6 | 340 | 19.26 | 65.22 | 0.21 | 0.00 | 43.84 | 6.00 | 0.18 | 3.34 | 46.30 | 53.70 |
| 23.1 | 340 | 13.66 | 91.97 | 0.20 | 0.00 | 43.91 | 5.94 | 0.18 | 3.64 | 45.99 | 54.01 |
| 23.8 | 340 | 21.62 | 58.10 | 0.21 | 0.00 | 43.73 | 5.95 | 0.18 | 3.24 | 46.55 | 53.45 |
| 25.6 | 340 | 31.11 | 40.39 | 0.22 | 0.00 | 43.48 | 5.99 | 0.19 | 3.04 | 46.96 | 53.04 |
| 26.4 | 340 | 21.06 | 59.67 | 0.21 | 0.00 | 43.74 | 5.95 | 0.19 | 2.91 | 46.87 | 53.13 |
| 27.6 | 340 | 31.31 | 40.13 | 0.21 | 0.00 | 43.72 | 6.00 | 0.18 | 3.08 | 46.67 | 53.33 |
| 28.3 | 340 | 22.32 | 56.29 | 0.20 | 0.00 | 43.62 | 5.94 | 0.18 | 3.36 | 46.56 | 53.44 |
| 29.6 | 340 | 20.19 | 62.23 | 0.22 | 0.00 | 44.37 | 6.11 | 0.18 | 2.83 | 46.16 | 53.84 |
| 30.4 | 340 | 24.61 | 51.06 | 0.23 | 0.00 | 44.21 | 6.13 | 0.19 | 2.84 | 46.27 | 53.73 |
| 31.5 | 340 | 24.69 | 50.88 | 0.21 | 0.00 | 43.96 | 6.09 | 0.18 | 3.57 | 45.85 | 54.15 |
| 32.8 | 340 | 15.03 | 83.58 | 0.21 | 0.00 | 43.97 | 6.03 | 0.18 | 3.04 | 46.42 | 53.58 |
| 34.3 | 340 | 14.53 | 86.48 | 0.21 | 0.00 | 44.47 | 6.08 | 0.18 | 3.20 | 45.70 | 54.30 |
| 36.1 | 340 | 19.60 | 64.11 | 0.22 | 0.00 | 44.04 | 6.05 | 0.19 | 3.03 | 46.45 | 53.55 |
| 52.8 | 340 | 22.87 | 54.94 | 0.23 | 0.00 | 44.15 | 6.18 | 0.18 | 2.24 | 46.89 | 53.11 |
| 54.3 | 340 | 23.27 | 53.99 | 0.23 | 0.00 | 43.82 | 6.07 | 0.18 | 2.24 | 47.34 | 52.66 |
| 56.9 | 340 | 22.48 | 55.90 | 0.22 | 0.00 | 43.83 | 6.07 | 0.18 | 2.33 | 47.23 | 52.77 |
| 58.8 | 340 | 20.36 | 61.70 | 0.22 | 0.00 | 43.86 | 6.07 | 0.18 | 2.57 | 46.96 | 53.04 |
| 60.0 | 340 | 19.50 | 64.44 | 0.22 | 0.00 | 44.16 | 6.11 | 0.18 | 2.38 | 46.82 | 53.18 |
| 76.6 | 340 | 21.11 | 59.51 | 0.23 | 0.00 | 44.14 | 6.20 | 0.18 | 1.96 | 47.16 | 52.84 |

TABLE 10-continued

HFC-236ea→HFC-1225ye coking study at 340° C. and 5 barg in the absence of co-fed HF

| | | | | Normalised mole % | | | | | | | | |
|---|---|---|---|---|---|---|---|---|---|---|---|---|
| Time (hrs) | Temperature (° C.) | 236ea (ml/min) | CT (sec) | 1234yf | 1225zc | Z-1225ye | E-1225ye | 227ea | 236cb | 236ee | 236ee conversion (%) | |
| 78.6 | 340 | 22.90 | 54.86 | 0.23 | 0.00 | 43.95 | 6.19 | 0.18 | 2.00 | 47.33 | 52.67 | |
| 80.6 | 340 | 26.29 | 47.80 | 0.23 | 0.00 | 43.87 | 6.16 | 0.18 | 1.97 | 47.47 | 52.53 | |
| 81.8 | 340 | 21.51 | 58.41 | 0.23 | 0.00 | 43.42 | 6.11 | 0.18 | 1.71 | 48.22 | 51.78 | |
| 83.6 | 340 | 22.41 | 56.06 | 0.22 | 0.00 | 44.11 | 6.13 | 0.18 | 2.55 | 46.69 | 53.31 | |
| 100.8 | 340 | 29.37 | 42.78 | 0.23 | 0.00 | 43.52 | 6.16 | 0.18 | 1.66 | 48.13 | 51.87 | |
| 101.8 | 340 | 13.36 | 94.05 | 0.23 | 0.00 | 43.96 | 6.16 | 0.18 | 1.74 | 47.59 | 52.41 | |
| 103.3 | 340 | 23.20 | 54.16 | 0.22 | 0.00 | 43.61 | 6.15 | 0.18 | 2.40 | 47.30 | 52.70 | |
| 104.9 | 340 | 22.83 | 55.05 | 0.22 | 0.00 | 43.33 | 6.02 | 0.18 | 2.02 | 48.09 | 51.91 | |
| 106.5 | 340 | 16.79 | 74.81 | 0.22 | 0.00 | 43.75 | 6.20 | 0.18 | 2.23 | 47.29 | 52.71 | |
| 108.2 | 340 | 17.36 | 72.37 | 0.23 | 0.00 | 44.11 | 6.17 | 0.18 | 1.92 | 47.26 | 52.74 | |
| 124.6 | 340 | 19.78 | 63.51 | 0.23 | 0.00 | 43.78 | 6.22 | 0.18 | 1.62 | 47.84 | 52.16 | |
| 125.9 | 340 | 27.77 | 45.25 | 0.23 | 0.00 | 43.53 | 6.18 | 0.18 | 1.51 | 48.23 | 51.77 | |
| 127.3 | 340 | 19.68 | 63.83 | 0.22 | 0.00 | 44.07 | 6.19 | 0.18 | 2.00 | 47.22 | 52.78 | |
| 128.8 | 340 | 22.98 | 54.68 | 0.23 | 0.00 | 42.82 | 6.03 | 0.18 | 1.27 | 49.34 | 50.66 | |
| 130.1 | 340 | 25.12 | 50.01 | 0.23 | 0.00 | 43.25 | 6.14 | 0.18 | 1.39 | 48.68 | 51.32 | |

Surprisingly, the catalyst performance was good and steady over a period of 120 hours, with no indication of fouling. The experiment was repeated at 10 barg; the results are shown in Table 11.

TABLE 11

HFC-236ea→HFC-1225ye coking study at 340° C. and 10 barg in the absence of co-fed HF

| | | | | | Normalised mol % | | | | | | | |
|---|---|---|---|---|---|---|---|---|---|---|---|---|
| Time (hrs) | Temp (° C.) | 236ea (ml/min) | N2 Diluent (ml/min) | Contact time (sec) | 1234yf | 1225zc | Z-1225ye | E-1225ye | 227ea | 236cb | 236ee | 236ea conv (%) |
| 0.42 | 340 | 11.44 | 0 | 201.30 | 0.16 | 0.01 | 42.71 | 5.60 | 0.94 | 8.44 | 41.94 | 58.06 |
| 1.00 | 340 | 18.02 | 0 | 127.84 | 0.16 | 0.00 | 34.62 | 4.67 | 0.58 | 6.32 | 53.30 | 46.70 |
| 2.00 | 340 | 14.83 | 0 | 155.27 | 0.16 | 0.00 | 34.32 | 4.73 | 0.37 | 5.85 | 54.40 | 45.60 |
| 3.00 | 340 | 17.56 | 0 | 131.16 | 0.16 | 0.00 | 34.14 | 4.72 | 0.34 | 5.50 | 54.87 | 45.13 |
| 4.33 | 340 | 18.31 | 0 | 125.82 | 0.16 | 0.00 | 34.30 | 4.72 | 0.32 | 5.25 | 54.98 | 45.02 |
| 5.33 | 340 | 11.85 | 0 | 194.41 | 0.17 | 0.00 | 34.43 | 4.72 | 0.31 | 5.01 | 55.20 | 44.80 |
| 22.00 | 340 | 22.35 | 0 | 103.05 | 0.18 | 0.00 | 34.40 | 4.81 | 0.25 | 3.52 | 56.69 | 43.31 |
| 23.17 | 340 | 15.13 | 0 | 152.25 | 0.17 | 0.00 | 34.30 | 4.81 | 0.25 | 3.47 | 56.83 | 43.17 |
| 24.25 | 340 | 9.41 | 0 | 244.76 | 0.17 | 0.00 | 34.28 | 4.76 | 0.25 | 3.66 | 56.72 | 43.28 |
| 25.33 | 340 | 19.27 | 0 | 119.55 | 0.17 | 0.00 | 34.23 | 4.79 | 0.25 | 3.61 | 56.77 | 43.23 |
| 25.83 | 340 | 17.59 | 0 | 130.93 | 0.17 | 0.00 | 34.18 | 4.77 | 0.25 | 3.68 | 56.77 | 43.23 |
| 43.33 | 340 | 19.63 | 0 | 117.37 | 0.17 | 0.00 | 34.44 | 4.85 | 0.24 | 2.99 | 57.13 | 42.87 |
| 44.25 | 340 | 21.35 | 0 | 107.90 | 0.18 | 0.00 | 34.30 | 4.80 | 0.24 | 2.89 | 57.40 | 42.60 |
| 44.83 | 340 | 6.81 | 40 | 49.20 | 0.24 | 0.00 | 48.89 | 6.78 | 0.16 | 2.33 | 41.46 | 58.54 |
| 45.67 | 340 | 19.86 | 40 | 38.48 | 0.25 | 0.00 | 49.22 | 6.91 | 0.15 | 2.44 | 40.89 | 59.11 |
| 46.50 | 340 | 19.31 | 40 | 38.84 | 0.25 | 0.00 | 49.66 | 6.95 | 0.15 | 2.49 | 40.36 | 59.64 |
| 47.08 | 340 | 20.01 | 40 | 38.38 | 0.25 | 0.00 | 49.84 | 6.96 | 0.15 | 2.52 | 40.14 | 59.86 |
| 47.67 | 340 | 18.11 | 80 | 23.48 | 0.29 | 0.00 | 57.01 | 8.00 | 0.11 | 2.24 | 32.23 | 67.77 |
| 48.17 | 340 | 13.42 | 80 | 24.66 | 0.29 | 0.00 | 57.83 | 8.08 | 0.11 | 2.19 | 31.39 | 68.61 |
| 49.08 | 340 | 14.09 | 80 | 24.48 | 0.29 | 0.00 | 58.00 | 8.10 | 0.11 | 2.22 | 31.16 | 68.84 |
| 49.75 | 340 | 9.15 | 80 | 25.84 | 0.28 | 0.00 | 58.19 | 8.09 | 0.11 | 2.19 | 31.02 | 68.98 |
| 50.33 | 340 | 15.74 | 80 | 24.06 | 0.29 | 0.00 | 57.91 | 8.10 | 0.10 | 2.20 | 31.27 | 68.73 |
| 67.00 | 340 | 15.51 | 80 | 24.12 | 0.29 | 0.00 | 56.89 | 8.01 | 0.11 | 1.85 | 32.73 | 67.27 |
| 68.00 | 340 | 16.00 | 120 | 16.94 | 0.31 | 0.00 | 61.18 | 8.69 | 0.08 | 1.70 | 27.92 | 72.08 |
| 68.50 | 340 | 16.84 | 120 | 16.83 | 0.31 | 0.00 | 61.36 | 8.70 | 0.08 | 1.68 | 27.76 | 72.24 |
| 69.25 | 340 | 17.19 | 120 | 16.79 | 0.31 | 0.00 | 61.25 | 8.66 | 0.08 | 1.69 | 27.90 | 72.10 |
| 71.00 | 340 | 8.67 | 120 | 17.90 | 0.32 | 0.00 | 62.48 | 8.73 | 0.08 | 1.62 | 26.67 | 73.33 |
| 71.75 | 340 | 6.65 | 160 | 13.82 | 0.32 | 0.00 | 64.92 | 9.09 | 0.07 | 1.47 | 24.04 | 75.96 |
| 72.42 | 340 | 16.04 | 160 | 13.08 | 0.32 | 0.00 | 64.25 | 9.10 | 0.07 | 1.51 | 24.65 | 75.35 |
| 73.42 | 340 | 1.08 | 160 | 14.30 | 0.31 | 0.00 | 65.22 | 9.07 | 0.07 | 1.49 | 23.76 | 76.24 |
| 73.75 | 340 | 14.16 | 80 | 24.46 | 0.29 | 0.00 | 57.90 | 8.13 | 0.10 | 1.81 | 31.64 | 68.36 |
| 74.25 | 340 | 13.86 | 80 | 24.54 | 0.29 | 0.00 | 57.85 | 8.11 | 0.10 | 1.75 | 31.76 | 68.24 |
| 90.83 | 340 | 12.41 | 80 | 24.93 | 0.30 | 0.00 | 56.63 | 7.96 | 0.11 | 1.55 | 33.34 | 66.66 |
| 91.50 | 340 | 17.07 | 80 | 23.73 | 0.30 | 0.00 | 55.51 | 7.85 | 0.11 | 1.48 | 34.63 | 65.37 |
| 92.17 | 340 | 14.69 | 80 | 24.33 | 0.30 | 0.00 | 54.69 | 7.75 | 0.12 | 1.34 | 35.68 | 64.32 |
| 93.00 | 340 | 19.05 | 80 | 23.26 | 0.29 | 0.00 | 54.76 | 7.80 | 0.12 | 1.40 | 35.53 | 64.47 |
| 93.75 | 340 | 24.15 | 80 | 22.12 | 0.29 | 0.00 | 53.91 | 7.71 | 0.12 | 1.39 | 36.46 | 63.54 |
| 95.17 | 340 | 21.02 | 80 | 22.80 | 0.29 | 0.00 | 54.49 | 7.73 | 0.12 | 1.38 | 35.88 | 64.12 |
| 96.00 | 340 | 21.25 | 80 | 22.75 | 0.29 | 0.00 | 52.93 | 7.57 | 0.12 | 1.27 | 37.70 | 62.30 |
| 97.17 | 340 | 15.94 | 80 | 24.01 | 0.29 | 0.00 | 53.70 | 7.63 | 0.12 | 1.26 | 36.87 | 63.13 |

At the higher pressure, the conversion rate was somewhat lower, again reflecting the HF inhibition. The impact after feed dilution can be seen after 44.25 hours, when nitrogen was added to the HFC-236ea feed. Again over the course of the whole experiment there was little sign of catalyst fouling.

EXAMPLE 12

This example demonstrates the beneficial effect of diluting the feed (e.g. HFC-236ea) during catalytic conversion at pressure with a recycled material in the context of the process, e.g. an E/Z isomer mix of the resultant HFC-1225ye product, or an isomer rich blend of HFC-1225ye (by isomer rich is meant a blend of E and Z isomers which differs from that which had been normally produced as a result of the process. The isomer rich blend could for example comprise a blend of E and Z isomers which contains a higher level of either E or Z isomer than would normally be thermodynamically formed, or it could contain either pure E isomer or pure Z isomer, conveniently pure Z isomer).

In the example, HFC-236ea feed was diluted with Z-HFC-1225ye in the ratio 30:70. The blend was passed over freshly regenerated catalyst at 340° C. and 10 barg. The results are summarised in Table 12.

It was found that the "per pass" HFC-236ea conversion was lower than with nitrogen diluents. It was concluded recycled HFC-1225ye in whatever isomer blend desired could be utilised to dilute the HFC-236ea feed and produce superior catalytic conversion of HFC-236ea to e.g. Z-HFC-1225ye.

EXAMPLE 13

Vapour Phase Isomerisation Over 6% Zn/Chromia in the Absence of HF Including Catalyst Regeneration A 2 g sample of amorphous 6.0% Zn/chromia catalyst was charged to a 15 cm×1.25 cm Inconnel reactor tube. The catalyst was dried (250° C. for 1 hour) and pre-fluorinated (N2: HF molar ratio of 6:1 for 1 hour at 250° C., temperature ramped to 380° C., nitrogen diluent switched off and left overnight). Following pre-fluorination the reactor was cooled. Then a mixture of 5 ml/min nitrogen and 1 ml/min of a mixture of 87.8% E-HFC-1225ye, 9.1% Z-HFC-1225ye, and the balance being a mixture of minor amounts of HFC-227ea, HFC-236ea, HFC-236cb and hexafluoropropene was passed over the catalyst at 130° C. at 5 ml/min whilst monitoring the conversion of the E-isomer to the Z-isomer. After the conversion began to drop, the feed flow was stopped and the catalyst regenerated using a mixture of nitrogen (40 ml/min) and air (4 ml/min) at 380° C. for 12-16 hours. At the end of the regeneration the air feed was switched off and the catalyst was cooled to 130° C. When the catalyst had cooled the isomerisation cycle was repeated. The results of this isomerisation/regeneration/isomerisation cycle are presented in Table 13 below.

TABLE 12

HFC-236ea→HFC-1225ye coking study at 340° C. and 10 barg in the absence of co-fed HF using HFC-1225ye as a diluent

| Time (hrs) | Temp (° C.) | Total orgs (ml/min) | 1225ye (ml/min) | 236ea (ml/min) | CT (sec) | Normalised mole % | | | | | | | 236ea conv (%) |
| --- | --- | --- | --- | --- | --- | --- | --- | --- | --- | --- | --- | --- | --- |
| | | | | | | 1234yf | 1225zc | Z-1225ye | E-1225ye | 227ea | 236cb | 236ee | |
| 18.75 | 340 | 32.20 | 22.54 | 9.66 | 71.53 | 0.06 | 0.20 | 65.41 | 9.00 | 0.02 | 5.66 | 19.29 | 35.71 |
| 19.33 | 340 | 30.24 | 21.17 | 9.07 | 76.17 | 0.06 | 0.20 | 65.66 | 8.98 | 0.02 | 5.51 | 19.20 | 35.99 |
| 20.25 | 340 | 32.09 | 22.46 | 9.63 | 71.78 | 0.06 | 0.20 | 65.48 | 8.95 | 0.02 | 5.47 | 19.37 | 35.42 |
| 21.25 | 340 | 33.40 | 23.38 | 10.02 | 68.97 | 0.06 | 0.21 | 65.79 | 9.01 | 0.02 | 5.39 | 19.10 | 36.32 |
| 22.92 | 340 | 26.94 | 18.86 | 8.08 | 85.51 | 0.06 | 0.20 | 65.88 | 8.95 | 0.03 | 5.44 | 19.02 | 36.61 |
| 24.92 | 340 | 30.88 | 21.62 | 9.26 | 74.59 | 0.06 | 0.20 | 65.43 | 9.00 | 0.03 | 5.55 | 19.28 | 35.73 |
| 25.92 | 340 | 19.02 | 13.31 | 5.71 | 121.11 | 0.06 | 0.21 | 66.19 | 8.96 | 0.03 | 5.37 | 18.79 | 37.36 |
| 42.58 | 340 | 21.40 | 14.98 | 6.42 | 107.61 | 0.06 | 0.20 | 66.07 | 9.04 | 0.03 | 5.12 | 19.02 | 36.61 |
| 43.25 | 340 | 22.10 | 15.47 | 6.63 | 104.24 | 0.06 | 0.20 | 65.69 | 8.96 | 0.03 | 5.06 | 19.53 | 34.91 |
| 44.17 | 340 | 22.53 | 15.77 | 6.76 | 102.25 | 0.06 | 0.20 | 65.93 | 9.00 | 0.03 | 4.95 | 19.33 | 35.56 |
| 45.75 | 340 | 25.76 | 18.03 | 7.73 | 89.42 | 0.06 | 0.21 | 66.14 | 9.08 | 0.03 | 5.03 | 19.03 | 36.57 |
| 49.58 | 340 | 24.29 | 17.00 | 7.29 | 94.82 | 0.06 | 0.20 | 65.52 | 9.01 | 0.04 | 5.05 | 19.61 | 34.63 |
| 67.25 | 340 | 23.16 | 16.21 | 6.95 | 99.48 | 0.07 | 0.20 | 65.55 | 9.04 | 0.03 | 4.34 | 20.27 | 32.44 |
| 68.67 | 340 | 16.73 | 11.71 | 5.02 | 137.67 | 0.06 | 0.22 | 67.33 | 9.11 | 0.04 | 4.01 | 18.77 | 37.44 |
| 69.58 | 340 | 20.52 | 14.36 | 6.16 | 112.25 | 0.06 | 0.21 | 66.19 | 9.08 | 0.04 | 4.54 | 19.38 | 35.39 |
| 71.00 | 340 | 15.58 | 10.91 | 4.67 | 147.86 | 0.06 | 0.21 | 66.35 | 9.09 | 0.04 | 4.51 | 19.24 | 35.87 |
| 72.00 | 340 | 22.78 | 15.94 | 6.83 | 101.14 | 0.07 | 0.21 | 66.09 | 9.07 | 0.04 | 4.36 | 19.67 | 34.44 |
| 73.33 | 340 | 16.16 | 11.31 | 4.85 | 142.53 | 0.07 | 0.21 | 66.48 | 9.03 | 0.03 | 4.24 | 19.45 | 35.16 |
| 90.75 | 340 | 21.73 | 15.21 | 6.52 | 106.00 | 0.06 | 0.20 | 66.00 | 9.05 | 0.04 | 4.11 | 19.96 | 33.45 |
| 92.00 | 340 | 16.34 | 11.44 | 4.90 | 140.94 | 0.07 | 0.20 | 66.27 | 9.04 | 0.03 | 3.57 | 20.32 | 32.27 |
| 94.83 | 340 | 5.38 | 3.77 | 1.61 | 428.00 | 0.04 | 0.21 | 67.75 | 8.93 | 0.07 | 4.79 | 17.51 | 41.62 |
| 95.58 | 340 | 10.27 | 7.19 | 3.08 | 224.34 | 0.04 | 0.21 | 67.05 | 8.95 | 0.07 | 4.87 | 18.06 | 39.79 |
| 96.25 | 340 | 9.34 | 6.53 | 2.80 | 246.75 | 0.05 | 0.20 | 66.03 | 8.81 | 0.07 | 5.04 | 19.06 | 36.45 |
| 97.25 | 340 | 8.82 | 6.17 | 2.65 | 261.14 | 0.05 | 0.20 | 64.93 | 8.73 | 0.07 | 5.19 | 20.14 | 32.87 |
| 100.50 | 340 | 16.28 | 11.40 | 4.89 | 141.46 | 0.07 | 0.21 | 66.84 | 9.10 | 0.08 | 3.44 | 19.66 | 34.48 |
| 101.58 | 340 | 17.09 | 11.97 | 5.13 | 134.76 | 0.06 | 0.22 | 65.59 | 9.03 | 0.08 | 4.50 | 19.80 | 33.99 |
| 103.92 | 340 | 9.05 | 6.34 | 2.72 | 254.43 | 0.06 | 0.21 | 65.51 | 8.91 | 0.07 | 4.32 | 20.28 | 32.38 |
| 106.25 | 340 | 22.83 | 15.98 | 6.85 | 100.89 | 0.05 | 0.21 | 65.50 | 9.02 | 0.08 | 4.63 | 19.75 | 34.17 |

TABLE 13

| Time (mins) | HFC-1225ye isomeric composition % | |
|---|---|---|
| | Z-1225ye | E-1225ye |
| Cycle 1: | | |
| 8 | 91.4 | 3.8 |
| 43 | 94.4 | 3.8 |
| 63 | 94.6 | 3.7 |
| 93 | 94.5 | 3.7 |
| 119 | 94.5 | 3.9 |
| 155 | 94.6 | 3.9 |
| 181 | 92.0 | 3.7 |
| 213 | 93.1 | 4.0 |
| 298 | 89.1 | 9.5 |
| 335 | 85.7 | 12.6 |
| 358 | 79.7 | 19.2 |
| 378 | 76.5 | 22.0 |
| Cycle 2: | | |
| 10 | 95.0 | 3.7 |
| 35 | 94.4 | 3.7 |
| 70 | 94.6 | 3.8 |
| 95 | 94.4 | 3.8 |
| 125 | 94.6 | 3.8 |
| 150 | 94.7 | 3.9 |
| 185 | 94.3 | 4.1 |
| 215 | 94.0 | 4.7 |
| 241 | 91.7 | 7.0 |
| 270 | 86.0 | 12.5 |
| 300 | 75.0 | 23.4 |

These experiments demonstrated that the catalyst retained its isomerisation activity for a significant period in the absence of HF, the isomerisation performance began to deteriorate after 4-5 hrs of contacting, and an air/nitrogen regeneration restored the catalyst to its original state; therefore it can be concluded the loss of performance was due to coking-type reactions.

EXAMPLE 14

This example demonstrates how catalyst fouling rate can vary during the conversion of HFC-236ea to HFC-1225ye as a function of pressure. 6 g (2.0-3.5 mm) of a 5.2% Zn chromia catalyst was charged to a reactor and pre-fluorination by drying it at 250° C. overnight under 80 ml/min nitrogen at 3 Barg, heating it at 300° C. and treating it with 4 ml/min HF and 80 ml/min nitrogen at 3 Barg for 16 hours, reducing the nitrogen flow to zero and maintaining it at 300° C. for a further 4 hours, increasing the temperature to 380° C. at a rate of 25° C./hour and maintaining it at 380° C. for a further 3 hours.

At the end of the pre-fluorination, the reactor temperature was set to 340° C. and the pressure set to 15 Barg. HFC-236ea feed commenced when the conditions had stabilised. The target feed rate was 13-14 ml/min at STP. The reactor off-gases were routinely sampled to monitor catalyst performance. The cycle was ended when the performance of the catalyst was approximately half of the initial performance. The catalyst was regenerated at 380° C. with a mixture of air (4 ml/min) and nitrogen (80 ml/min). Three such experimental cycles were completed at 15, 5 and 2.3 Barg (3.3 Bara).

The actual mass of 236ea estimated to have been fed during each cycle was:

236ea fed during Cycle 1 at 15 Barg=1860 g

236ea fed during Cycle 1 at 5 Barg=1637 g

236ea fed during Cycle 1 at 2.3 Barg=1540 g

Results

Figure 6:
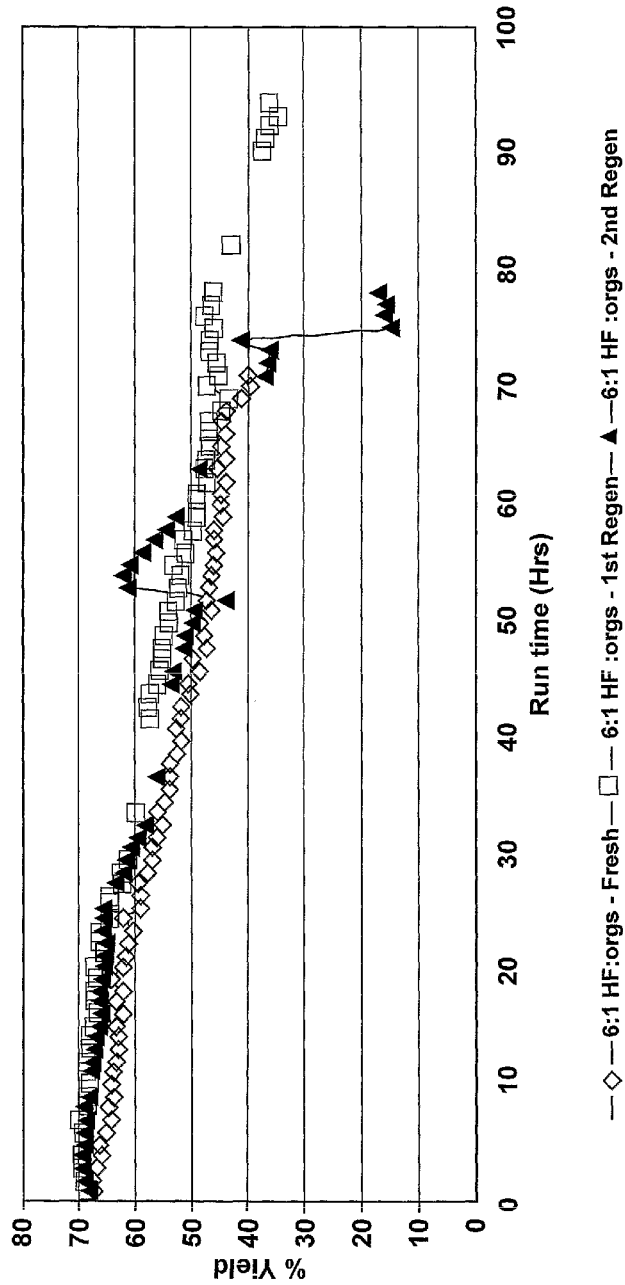
FIG. 6 is a graphical representation of the yield of Z-1225ye at a feed rate of 6HF:1 236ea over various run times.
Figure 7:
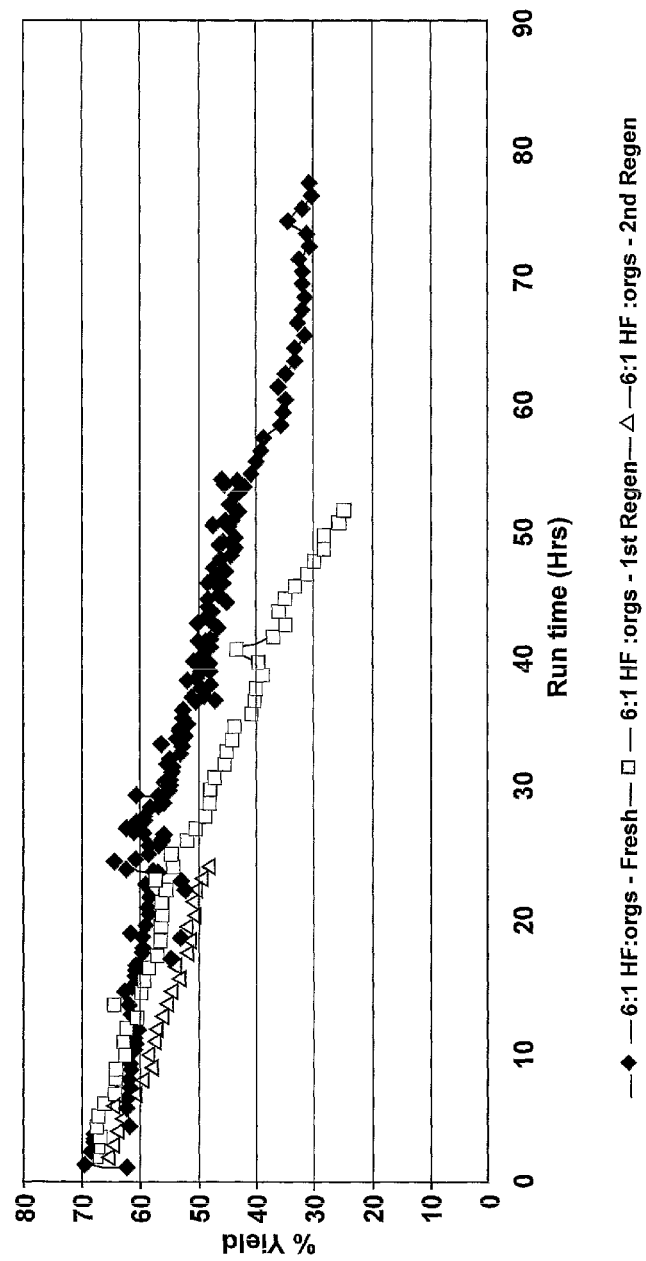
FIG. 7 is a graphical representation of the yield of Z-1225ye at a various feed rates of 6HF:1 236ea, depicting the fouling rate of these feed rates over various run times.

The results for each cycle at the different pressures are summarised in Tables 14-16 and illustrated in FIGS. 6-7.

As the pressure reduced, the headline conversion increased, reflecting the inhibiting effects of HF partial pressure on the reaction rate. This increased conversion as pressure reduced was even more pronounced when consideration was given to the reduction in contact time that occurred as the pressure was reduced.

At 15 and 5 Barg, the rate of performance loss and therefore fouling appeared similar. Furthermore, the rate of fouling appeared to accelerate as the tests progressed. At the lowest pressure tested, 2.3 Barg (3.3 Bara), the rate of fouling appeared to be marginally reduced. At low pressures, conversion was higher and therefore the catalyst was exposed to more unsaturates apparently without any detrimental effect on fouling rates.

FIG. 7 illustrates the selectivity to E and Z 1225ye during each cycle at the 3 different operating pressures. At 15 Barg the selectivity appeared to rise, stabilise and then fall away over the cycle. At 5 Barg a similar pattern of behavior was observed, although both the initial rise and final fall were less pronounced. At 2.3 Barg the selectivity was very stable over the cycle, with no apparent fall away.

The results suggest that catalyst fouling was not strongly pressure dependent, but selectivity was maintained at low operating pressures.

TABLE 14

Conversion and selectivity data at 340° C. and 15 Barg

| Time (hrs) | Selectivity (%) | 236ea Conversion (%) |
|---|---|---|
| 0.4 | 91.9 | 35.6 |
| 1.1 | 90.1 | 37.9 |
| 2.5 | 87.4 | 39.2 |
| 3.0 | 86.1 | 39.4 |
| 3.9 | 88.0 | 38.7 |
| 22.6 | 89.5 | 28.2 |
| 27.2 | 89.7 | 38.1 |
| 30.3 | 90.1 | 37.9 |
| 46.7 | 91.8 | 37.0 |
| 52.7 | 91.3 | 37.3 |
| 53.5 | 91.5 | 37.5 |
| 71.8 | 90.5 | 45.8 |
| 72.4 | 91.5 | 37.8 |
| 73.7 | 91.4 | 37.6 |
| 76.9 | 92.2 | 36.7 |
| 93.8 | 93.1 | 34.0 |
| 94.8 | 93.1 | 34.9 |
| 95.3 | 93.0 | 35.4 |
| 97.3 | 92.8 | 28.8 |
| 97.7 | 92.9 | 31.6 |
| 98.3 | 93.0 | 34.1 |
| 99.2 | 92.8 | 35.8 |
| 100.3 | 92.9 | 35.3 |
| 101.5 | 93.2 | 34.6 |
| 103.4 | 93.0 | 34.7 |
| 104.7 | 92.8 | 35.2 |
| 105.3 | 93.0 | 35.5 |
| 106.4 | 92.9 | 35.2 |
| 123.3 | 92.6 | 27.9 |
| 123.8 | 93.0 | 32.1 |
| 124.6 | 93.2 | 33.4 |
| 125.4 | 92.3 | 36.4 |
| 126.0 | 93.1 | 33.7 |
| 127.5 | 93.3 | 33.5 |
| 129.9 | 93.2 | 33.5 |
| 147.4 | 92.7 | 28.7 |
| 148.3 | 93.1 | 31.4 |
| 148.9 | 93.2 | 31.7 |

TABLE 14-continued

Conversion and selectivity data at 340° C. and 15 Barg

| Time (hrs) | Selectivity (%) | 236ea Conversion (%) |
|---|---|---|
| 152.8 | 93.2 | 31.9 |
| 174.3 | 92.4 | 30.6 |
| 176.1 | 93.1 | 31.6 |
| 178.6 | 93.0 | 29.5 |
| 195.9 | 92.7 | 28.1 |
| 196.6 | 92.7 | 27.8 |
| 202.3 | 92.8 | 26.9 |
| 202.8 | 95.6 | 47.8 |
| 204.6 | 92.3 | 26.0 |
| 205.6 | 92.3 | 25.9 |
| 249.0 | 87.2 | 14.4 |
| 250.5 | 86.3 | 15.9 |
| 274.5 | 84.9 | 14.5 |
| 275.5 | 87.3 | 14.6 |
| 277.7 | 91.2 | 20.7 |

TABLE 15

Conversion and selectivity data at 340° C. and 5 Barg

| Time (hrs) | Selectivity (%) | 236ea Conversion (%) |
|---|---|---|
| 0.7 | 94.2 | 53.6 |
| 1.4 | 94.7 | 51.8 |
| 2.2 | 94.5 | 51.2 |
| 18.6 | 95.5 | 47.9 |
| 20.0 | 95.0 | 52.3 |
| 20.4 | 95.4 | 48.0 |
| 22.1 | 95.4 | 47.8 |
| 22.9 | 92.9 | 54.8 |
| 23.8 | 95.5 | 44.4 |
| 25.0 | 95.4 | 46.3 |
| 25.9 | 95.3 | 49.9 |
| 27.7 | 95.3 | 49.3 |
| 28.7 | 95.3 | 51.8 |
| 29.6 | 95.1 | 49.8 |
| 31.2 | 95.2 | 50.6 |
| 47.9 | 95.4 | 50.6 |
| 48.6 | 95.4 | 49.9 |
| 50.0 | 95.5 | 49.4 |
| 55.3 | 95.4 | 50.1 |
| 71.9 | 95.6 | 48.6 |
| 72.8 | 95.5 | 47.4 |
| 73.7 | 95.4 | 49.3 |
| 75.8 | 95.1 | 51.7 |
| 96.6 | 95.6 | 49.2 |
| 97.0 | 95.6 | 48.8 |
| 97.8 | 95.6 | 47.3 |
| 98.4 | 95.6 | 47.1 |
| 99.7 | 95.5 | 47.8 |
| 100.9 | 95.6 | 43.0 |
| 101.8 | 95.7 | 45.7 |
| 119.0 | 95.6 | 46.5 |
| 119.4 | 95.7 | 46.5 |
| 120.9 | 95.6 | 45.8 |
| 123.0 | 95.6 | 44.7 |
| 123.9 | 95.7 | 44.8 |
| 125.8 | 95.6 | 43.7 |
| 192.3 | 94.4 | 33.5 |
| 192.8 | 94.2 | 33.1 |
| 193.4 | 94.4 | 33.9 |
| 195.3 | 95.0 | 34.9 |
| 196.1 | 94.5 | 34.5 |
| 215.4 | 94.4 | 33.7 |
| 216.3 | 93.5 | 28.5 |
| 217.6 | 92.8 | 25.1 |
| 219.0 | 93.0 | 26.3 |

TABLE 15-continued

Conversion and selectivity data at 340° C. and 5 Barg

| Time (hrs) | Selectivity (%) | 236ea Conversion (%) |
|---|---|---|
| 219.7 | 93.4 | 27.8 |
| 220.8 | 93.6 | 28.7 |
| 222.2 | 93.5 | 28.2 |
| 239.0 | 93.3 | 26.4 |
| 239.8 | 92.6 | 24.7 |
| 241.3 | 92.3 | 23.5 |

TABLE 16

Conversion and selectivity data at 340° C. and 2.3 Barg

| Time (hrs) | Selectivity (%) | 236ea Conversion (%) |
|---|---|---|
| 0.5 | 94.6 | 66.2 |
| 16.9 | 96.0 | 63.3 |
| 17.3 | 96.4 | 59.1 |
| 18.4 | 96.2 | 61.0 |
| 19.1 | 96.2 | 61.6 |
| 20.8 | 95.5 | 63.8 |
| 21.2 | 95.4 | 64.1 |
| 21.9 | 95.7 | 63.4 |
| 22.9 | 96.9 | 54.9 |
| 23.3 | 96.6 | 61.8 |
| 24.2 | 96.6 | 62.3 |
| 24.5 | 96.2 | 65.0 |
| 25.0 | 96.4 | 63.3 |
| 25.8 | 96.3 | 65.2 |
| 42.9 | 96.8 | 60.9 |
| 43.5 | 96.9 | 60.4 |
| 44.2 | 96.7 | 61.9 |
| 45.2 | 96.7 | 62.5 |
| 46.8 | 96.7 | 62.1 |
| 47.4 | 96.5 | 64.5 |
| 48.5 | 96.6 | 64.6 |
| 49.9 | 96.6 | 63.5 |
| 66.9 | 96.8 | 58.3 |
| 67.3 | 96.9 | 58.9 |
| 67.9 | 96.8 | 61.0 |
| 68.4 | 96.7 | 63.2 |
| 68.9 | 96.6 | 61.9 |
| 71.9 | 96.6 | 62.7 |
| 72.9 | 96.2 | 63.5 |
| 91.0 | 96.3 | 60.2 |
| 114.1 | 96.2 | 64.3 |
| 116.5 | 96.9 | 59.9 |
| 121.5 | 96.5 | 59.2 |
| 139.7 | 95.7 | 63.0 |
| 140.5 | 96.4 | 59.7 |
| 141.7 | 96.2 | 61.9 |
| 143.0 | 96.1 | 63.6 |
| 143.5 | 96.3 | 61.9 |
| 144.2 | 96.1 | 63.3 |
| 144.8 | 96.1 | 62.0 |
| 145.3 | 96.4 | 61.7 |
| 146.0 | 96.5 | 59.7 |
| 146.6 | 96.7 | 58.3 |
| 163.4 | 96.5 | 59.0 |
| 164.0 | 96.6 | 59.0 |
| 164.6 | 96.6 | 58.0 |
| 167.1 | 96.4 | 53.2 |
| 168.0 | 96.6 | 57.2 |
| 169.0 | 96.6 | 54.1 |
| 187.1 | 96.5 | 60.4 |
| 187.6 | 95.0 | 65.8 |
| 193.0 | 96.4 | 54.4 |
| 193.5 | 96.2 | 61.9 |
| 194.0 | 95.9 | 57.3 |

TABLE 16-continued

Conversion and selectivity data at 340° C. and 2.3 Barg

| Time (hrs) | Selectivity (%) | 236ea Conversion (%) |
|---|---|---|
| 213.9 | 96.1 | 42.7 |
| 244.0 | 96.0 | 41.0 |
| 244.6 | 96.0 | 41.1 |
| 245.7 | 96.1 | 41.6 |
| 250.7 | 96.3 | 47.3 |
| 267.2 | 96.3 | 46.3 |
| 267.6 | 96.3 | 45.3 |
| 271.5 | 96.0 | 42.4 |
| 291.2 | 96.2 | 44.9 |
| 295.7 | 95.0 | 39.8 |
| 297.2 | 95.9 | 39.2 |
| 315.1 | 95.8 | 38.9 |
| 315.9 | 95.7 | 37.5 |

We claim:

1. A process for preparing a $C_{3-6}$ (hydro)fluoroalkene comprising dehydrohalogenating a $C_{3-6}$ hydro(halo)fluoroalkane in the presence of a zinc/chromia catalyst, wherein the $C_{3-6}$ (hydro)fluoroalkene produced is isomerised in the presence of the zinc/chromia catalyst.

2. A process according to claim 1 wherein. the $C_{3-6}$ (hydro) fluoroalkene exists in E and Z isomers, and the ratio of E and Z isomers is changed in the presence of the zinc/chromia catalyst.

3. A process according to claim 2 wherein the presence of the zinc/chromia catalyst changes the ratio of E and Z isomers from that which is the kinematic determined mixture of isomers from the preparation of the $C_{3-6}$ (hydro)fluoroalkene.

4. A process according to claim 2 wherein a desired isomer of the $C_{3-6}$ (hydro)fluoroalkene is recovered in a subsequent step.

5. A process according to claim 1 carried out at a temperature of from −70 to 400 °C. and a pressure of from 0 to 30 bara.

6. A process according to claim 1 for preparing a (hydro) fluoropropene comprising dehydrohalogenating a hydro(halo)fluoropropane.

7. A process according to claim 6 wherein the (hydro) fluoropropene produced is selected from tetrafluoropropenes and pentafluoropropenes.

8. A process according claim 7 for preparing 1,2,3,3,3-pentafluoropropene ($CF_3CF=CHF$).

9. A process according to claim 7 for preparing 1,3,3,3-tetrafluoropropene ($CF_3CH=CHF$).

10. A process according to claim 7 for preparing 2,3,3,3-tetrafluoropropene ($CF_3CF=CH_2$) and 1,2,3,3,3-pentafluoropropene ($CF_3CF=CHF$).

11. A process according to claim 7 for preparing 2,3,3,3-tetrafluoropropene ($CF_3CF=CH_2$) and 1,3,3,3-tetrafluoropropene ($CF_3CH=CHF$).

12. A process according to claim 1 wherein the dehydrohalogenating step is carried out in the presence of a feed comprising hydrogen fluoride (HF).

13. A process according to claim 1 wherein the dehydrohalogenating step is carried out in the absence of added hydrogen fluoride.

14. A process according to claim 1 wherein the zinc chromia catalyst comprises 0.01% to 25% by weight zinc.

15. A process according to claim 1 wherein the zinc chromia catalyst is amorphous or from 0,1 to 50% by weight of the catalyst is in the form of one or more crystalline compounds of chromium and/ or more crystalline compounds of zinc.

16. A process according to claim 5 wherein the process is carried out in the vapour phase at a temperature of from 200 to 360° C.

17. A process according to claim 5 wherein the process is carried out at super-atmospheric pressure.

18. A process according to claim 1 wherein the process is carried out with a diluent gas.

19. A process according to claim 18 wherein the diluent gas comprises nitrogen.

20. A process according to claim 18 wherein the diluent gas comprises the resultant $C_{3-6}$ (hydro) fluoroalkene or an isomer rich blend of the $C_{3-6}$ hydro)fluoroalkene.

21. A process according to claim 1 wherein the process is carried out in the presence of HF and at atmospheric or sub-atmospheric pressure and wherein the ratio of HF to hydro(halo)fluoroalkane is greater than 1.5:1.

* * * * *